US012629041B2

(12) United States Patent　　　(10) Patent No.:　US 12,629,041 B2
Sakamoto et al.　　　　　　　　　(45) Date of Patent:　May 19, 2026

(54) VITAL INFORMATION ACQUISITION APPARATUS AND METHOD

(71) Applicant: MaRI Co., Ltd., Kyoto (JP)

(72) Inventors: Takuya Sakamoto, Nishikyo-ku (JP); Hirofumi Taki, Shimogyo-ku (JP); Shigeaki Okumura, Shimogyo-ku (JP); Shunsuke Iwata, Nishikyo-ku (JP); Takato Koda, Nishikyo-ku (JP)

(73) Assignee: MaRI Co., Ltd., Shimogyo-ku (JP)

( * ) Notice: Subject to any disclaimer, the term of this patent is extended or adjusted under 35 U.S.C. 154(b) by 450 days.

(21) Appl. No.: 17/905,228

(22) PCT Filed: Mar. 1, 2021

(86) PCT No.: PCT/IB2021/000113
§ 371 (c)(1),
(2) Date: Aug. 29, 2022

(87) PCT Pub. No.: WO2021/171091
PCT Pub. Date: Sep. 2, 2021

(65) Prior Publication Data

US 2023/0112537 A1　　Apr. 13, 2023

Related U.S. Application Data

(60) Provisional application No. 63/151,774, filed on Feb. 21, 2021, provisional application No. 63/143,905,
(Continued)

(51) Int. Cl.
*A61B 5/024*　　(2006.01)
*A61B 5/0507*　　(2021.01)
(Continued)

(52) U.S. Cl.
CPC ............ *A61B 5/024* (2013.01); *A61B 5/0507* (2013.01); *A61B 5/0816* (2013.01); *G01S 7/415* (2013.01); *G01S 13/0209* (2013.01)

(58) Field of Classification Search
CPC .......... A61B 5/024; A61B 5/05; A61B 5/0816
See application file for complete search history.

(56) References Cited

U.S. PATENT DOCUMENTS 5,840,028 A　*　11/1998　Chubachi ............. A61B 8/5223
　　　　　　　　　　　　　　　　　　　　　600/437
7,916,066 B1　　3/2011　Osterweil
(Continued)

FOREIGN PATENT DOCUMENTS

CN　　106054156　　10/2016
CN　　108226883 B　　6/2018
(Continued)

OTHER PUBLICATIONS

Johns Hopkins Medicine, "Vital Signs (Body Temperature, Pulse Rate, Respiration Rate, Blood Pressure)," 2019, https://web.archive.org/web/20191118175515/https://www.hopkinsmedicine.org/health/conditions-and-diseases/vital-signs-body-temperature-pulse-rate-respiration-rate-blood-pressure#exp (Year: 2019).*
(Continued)

*Primary Examiner* — William Kelleher
*Assistant Examiner* — Noah Yi Min Zhu
(74) *Attorney, Agent, or Firm* — McBee Moore & Vanik IP, LLC

(57)　　　ABSTRACT

A vital information acquisition apparatus includes an ultra-wideband millimeter-wave radar system which includes at least one transmitting antenna and at least one receiving antenna and is configured to transmit ultra-wideband milli-meter-waves to a subject and receive ultra-wideband milli-meter-waves reflected by the subject, and a controller
(Continued)

includes circuitry that converts a plurality of received ultra-wideband millimeter-waves to radar signals reflected by the subject, stores the radar signals, calculates the differential signals among the radar signals at each position, calculates the intensity of the differential signals at each position, and estimates respiratory intervals, heartbeat intervals and position of the subject.

20 Claims, 15 Drawing Sheets

Related U.S. Application Data filed on Jan. 31, 2021, provisional application No. 62/982,064, filed on Feb. 27, 2020.

(51) Int. Cl.

| | |
|---|---|
| *A61B 5/08* | (2006.01) |
| *G01S 7/41* | (2006.01) |
| *G01S 13/02* | (2006.01) |

(56) References Cited

U.S. PATENT DOCUMENTS

| | | | | | |
|---|---|---|---|---|---|
| 8,068,051 | B1 | | 11/2011 | Osterweil | |
| 10,310,073 | B1 | * | 6/2019 | Santra | A61B 5/0816 |
| 11,350,849 | B2 | * | 6/2022 | Nakata | A61B 5/4818 |
| 2008/0077015 | A1 | * | 3/2008 | Boric-Lubecke | G01S 13/888 600/453 |
| 2008/0200823 | A1 | * | 8/2008 | Cho | A61B 5/02055 600/521 |
| 2010/0152600 | A1 | | 6/2010 | Droitcour et al. | |
| 2010/0240999 | A1 | | 9/2010 | Droitcour et al. | |
| 2010/0249630 | A1 | | 9/2010 | Droitcour et al. | |
| 2010/0249633 | A1 | | 9/2010 | Droitcour et al. | |
| 2010/0292568 | A1 | | 11/2010 | Droitcour et al. | |
| 2013/0079606 | A1 | * | 3/2013 | McGonigle | A61B 5/14551 600/323 |
| 2016/0174099 | A1 | * | 6/2016 | Goldfain | A61B 5/6831 375/130 |
| 2016/0220756 | A1 | * | 8/2016 | Doyle | A61B 5/08 |
| 2017/0095170 | A1 | * | 4/2017 | Verkruijsse | A61B 5/02416 |
| 2018/0153427 | A1 | * | 6/2018 | Al-Jumaily | A61B 5/021 |
| 2018/0263502 | A1 | * | 9/2018 | Lin | G01S 7/415 |
| 2018/0279884 | A1 | | 10/2018 | Ahmad et al. | |
| 2019/0239815 | A1 | * | 8/2019 | Gallagher | G01S 7/415 |
| 2019/0383928 | A1 | * | 12/2019 | Kuwahara | G01S 13/343 |
| 2020/0077963 | A1 | * | 3/2020 | Mollazadeh | A61B 5/339 |
| 2020/0107789 | A1 | * | 4/2020 | Kwon | A61B 5/7278 |
| 2020/0187835 | A1 | * | 6/2020 | Choi | A61B 5/681 |
| 2020/0345642 | A1 | * | 11/2020 | Ghoshal | A61B 5/1135 |
| 2021/0393215 | A1 | * | 12/2021 | Xia | A61B 5/1116 |
| 2022/0313113 | A1 | * | 10/2022 | Cho | A61B 5/7203 |

FOREIGN PATENT DOCUMENTS

| | | | | |
|---|---|---|---|---|
| JP | WO2018220701 | A1 | | 4/2020 |
| WO | WO-2016205891 | A1 | * 12/2016 | A61B 5/0205 |

OTHER PUBLICATIONS

International Search Report and Written Opinion mailed on Oct. 13, 2021 in PCT/IB2021/000113 filed on Mar. 1, 2021 (therein, 22 pages).

Yang, Y. et al., "Multi-Breath: Separate Respiration Monitoring for Multiple Persons with UWB Radar", 2019 IEEE 43rd Annual Computer Software and Applications Conference (COMPSAC), vol. 1, Jul. 15, 2019, pp. 840-849, XP033610077.

Walterscheid, I. et al., "Contactless Respiration and Heartbeat Monitoring of Multiple People Using a 2-D Imaging Radar", 2019 41st Annual International Conference of The IEEE Engineering in Medicine and Biology Society (EMBC), IEEE, Jul. 23, 2019, pp. 3720-3725, XP033624900.

Rivera, N. et al., "Multi-Target Estimation Of Heart And Respiration Rates Using Ultra Wideband Sensors" Jan. 30, 2006, total 7 pages, XP055846086. URL:https://www.researchgate.net/profile/Christopher-Anderson-27/publication/228343954_Multi-target_estimation_of_heart_and_respiration_rates_using_ultra_wideband_sensors/links/55928dfd08aeie9cb4295228/Multi-target-estimation-of-heart-and-respiration-rates-using-ultraOwideband-sensors.pdf.

\* cited by examiner 706 ultra-wideband
millimeter-wave
radar A 708 ultra-wideband
millimeter-wave
radar B 1300 ultra-wideband
millimeter-wave
radar C 1302 ultra-wideband
millimeter-wave
radar D 706 ultra-wideband
millimeter-wave
radar A 708 ultra-wideband
millimeter-wave
radar B 1300 ultra-wideband
millimeter-wave
radar C

VITAL INFORMATION ACQUISITION APPARATUS AND METHOD

CROSS-REFERENCE TO RELATED APPLICATIONS

The present application is a 35 U.S.C. § 371 national stage patent application of International patent application PCT/IB2021/000113, filed on Mar. 1, 2021, which is based upon and claims the benefits of priority to U.S. Provisional Application No. 62/982,064, filed Feb. 27, 2020, U.S. Provisional Application No. 63/143,905, filed Jan. 31, 2021, and U.S. Provisional Application No. 63/151,774, filed Feb. 21, 2021. The entire contents of the above applications are incorporated herein by reference.

TECHNICAL FIELD

The present invention is directed to a vital information acquisition apparatus and method that estimate respiratory intervals, heartbeat intervals, and positions of subjects.

BACKGROUND ART

Vital information monitoring is very important in order to provide appropriate healthcare services to patients (PL 1, NPL 1). Recently, several millimeter-wave radar techniques (PL 2, NPL 2, NPL 3) have been reported for the acquisition of vital information including heart rate and respiratory interval.

Citation List Patent Literature

PL 1 Katsuya Nakagawa, et. al. Vital information measuring device, managing device, and vital information communication system, EP1887488A1.
PL 2 Milan Savic, et. al., MM-wave radar vital signs detection apparatus and method of operation, WO2015/174879A1.

Citation List Non Patent Literature

NPL 1 Sandy Rolfe, The importance of respiratory rate monitoring, British Journal of Nursing, 2019.
NPL 2 Zhicheng Yang, et. al., Monitoring vital signs using millimeter wave, MobiHoc' 16, 2016.
NPL 3 Takuya Sakamoto, Recent progress in millimeter-wave radar signal processing, 12th Global Symposium on Millimeter Waves, 2019.

SUMMARY OF THE INVENTION

According to an aspect of the present invention, a vital information acquisition apparatus includes an ultra-wideband millimeter-wave radar system which includes at least one transmitting antenna and at least one receiving antenna and is configured to transmit ultra-wideband millimeter-waves to a subject and receive ultra-wideband millimeter-waves reflected by the subject, and a controller including circuitry which converts received ultra-wideband millimeter-waves to radar signals reflected by the subject, store the radar signals, calculates the differential signals among the radar signals at each position, calculates the intensity of the differential signals at each position, and estimates respiratory intervals, heartbeat intervals and position of the subject.

BRIEF DESCRIPTION OF DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF EMBODIMENTS

Figure 1:
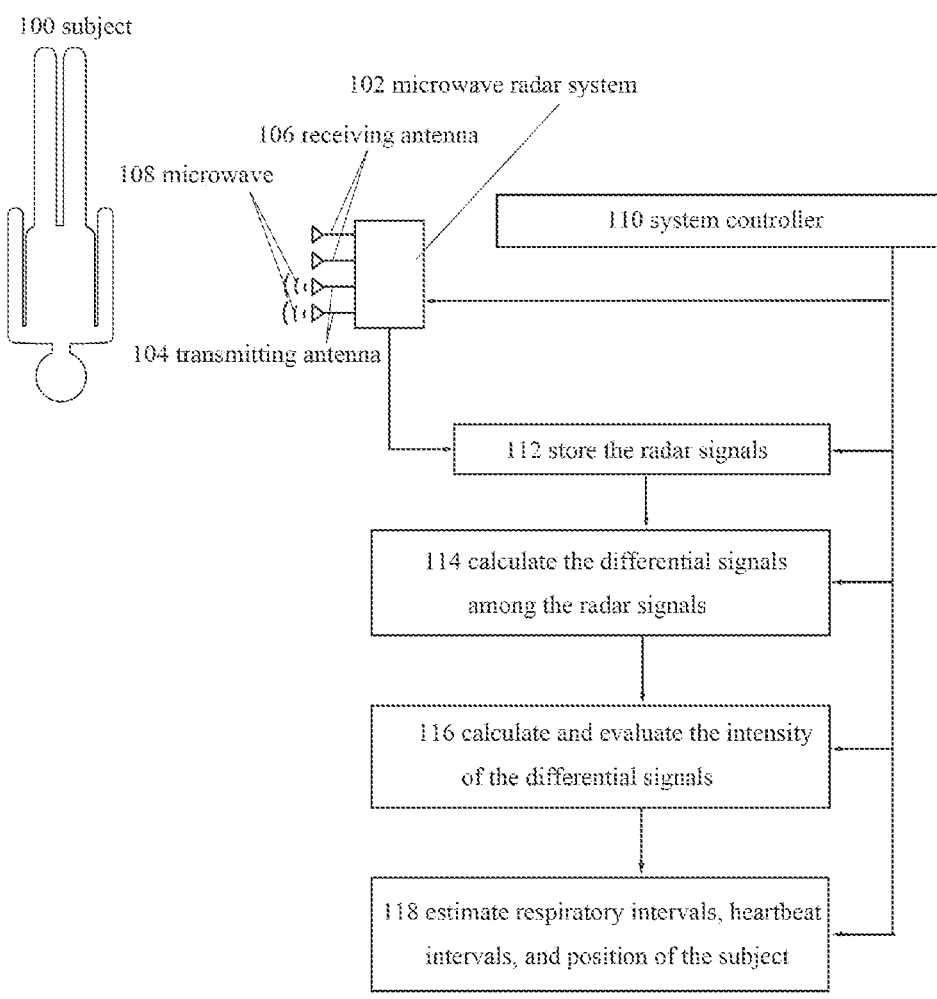
FIG. 1 is a schematic diagram of a vital information acquisition apparatus that transmits microwaves to a subject and estimates respiratory interval of the subject using the evaluation of differential signal intensity of radar signals.

The embodiments will now be described with reference to the accompanying drawings, wherein like reference numerals designate corresponding or identical elements throughout the various drawings.

Vital information acquisition apparatus according to an embodiment of the present invention transmits microwaves to a subject and estimates respiratory interval of the subject using the evaluation of differential signal intensity of radar signals. FIG. 1 shows a schematic diagram of a sleep apnea treatment apparatus employing an embodiment of the present invention. A microwave radar system 102 includes at least one transmitting antenna 104 and at least one receiving antenna 106. Microwaves 108 are transmitted from transmitting antennas 104. Transmitted microwave 108 can be modulated using one of pulse compression techniques, e.g. m-sequence. Transmitted microwaves are reflected at the body surface of a subject 100. Reflected microwaves are received by receiving antennas 106. A system controller 110 includes circuitry configured to convert a plurality of received microwaves to a plurality of radar signals, store the radar signals 112, calculate the differential signals among the radar signals 114, calculate and evaluate the intensity of the differential signals 116, and estimate respiratory intervals, heartbeat intervals, and position of the subject 118. A system controller 110 may be a computer that includes central processing unit (CPU) and a memory such as read-only memory (ROM) and random access memory (RAM). The CPU of the controller can be a single-core processor (which includes a single processing unit) or a multi-core processor. The computer may be a mobile device such as a personal digital assistant (PDA), laptop computer, field-programmable gate array, or cellular telephone. A computer, that includes central processing unit (CPU) and a memory such as read-only memory (ROM) and random access memory (RAM), may include a system controller 110. The system controller 110 may manage the passing and processing of the information. A system controller 110 or a computer may store the radar signals 112.

Figure 2:
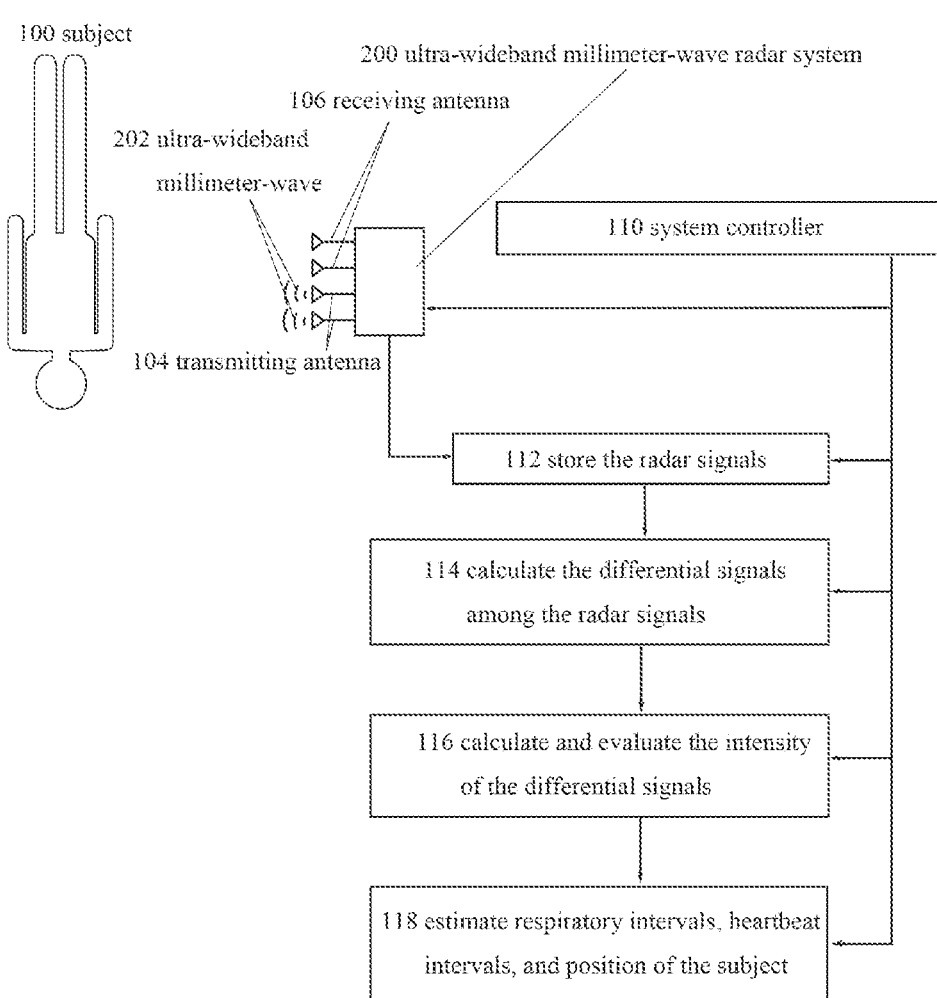
FIG. 2 is a schematic diagram of a vital information acquisition apparatus that transmits ultra-wideband millimeter-waves to a subject and estimates respiratory interval of the subject using the evaluation of differential signal intensity of radar signals.
Figure 3:
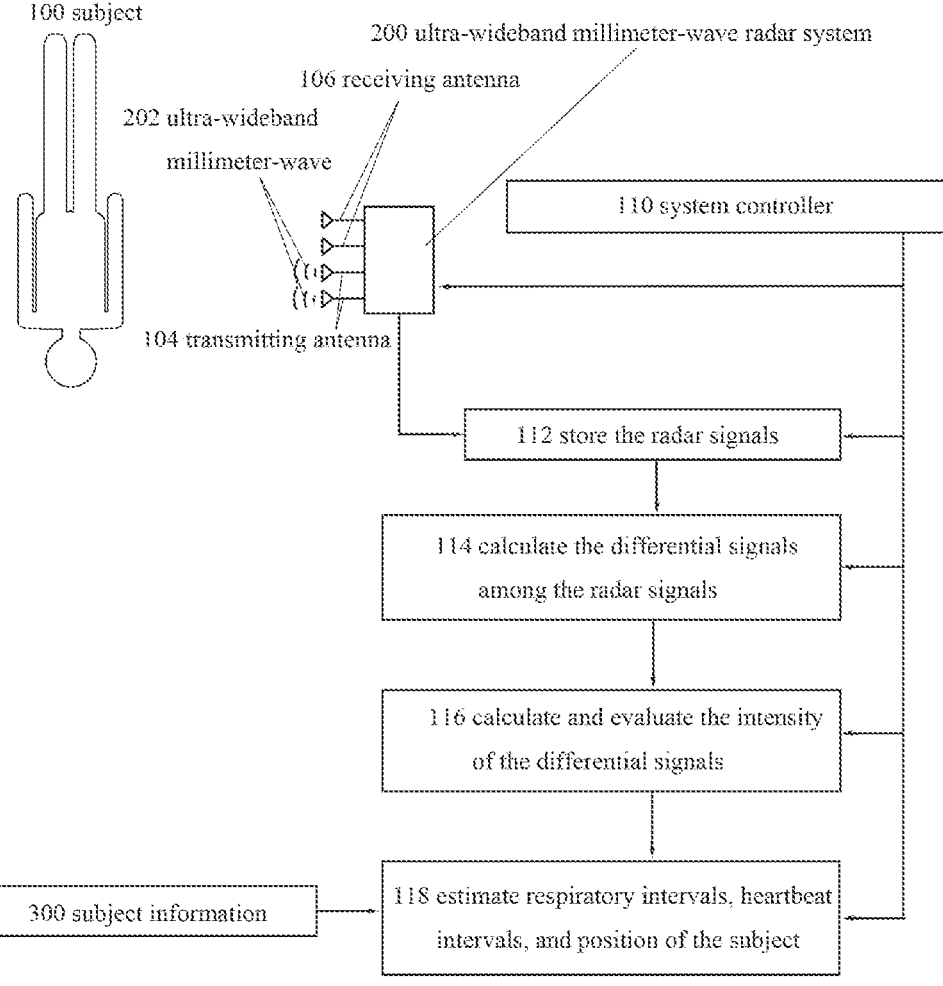
FIG. 3 is a schematic diagram of a vital information acquisition apparatus that transmits ultra-wideband millimeter-waves to a subject and estimates respiratory interval of the subject using the evaluation of differential signal intensity of radar signals, where the subject information is utilized to estimate respiratory intervals of the subject.

An ultra-wideband millimeter-wave radar system 200 can be used. FIG. 2 shows a schematic diagram of a sleep apnea treatment apparatus employing an embodiment of the present invention. An ultra-wideband millimeter-wave radar system 200 includes at least one transmitting antenna 104 and at least one receiving antenna 106. Ultra-wideband millimeter-waves 202 are transmitted from transmitting antennas 104. Transmitted ultra-wideband millimeter-wave 202 can be modulated using on of pulse compression techniques, e.g. m-sequence. Transmitted ultra-wideband millimeter-waves are reflected at the body surface of a subject 100. Reflected ultra-wideband millimeter-waves are received by receiving antennas 106. A system controller 110 includes circuitry configured to convert a plurality of received ultra-wideband millimeter-waves to a plurality of radar signals, store the radar signals 112, calculate the differential signals among the radar signals 114, calculate and evaluate the intensity of the differential signals 116, and estimate respiratory intervals, heartbeat intervals, and position of the subject 118. An ultra-wideband millimeter-wave radar system can detect and identify a plurality of subjects in the different distances.

For example, respiratory interval, heartbeat interval, and/or position of a subject can be estimated by the time difference which minimizes the intensity of the differential signals at each position. One example of the minimization of the intensity of the differential signal at a position is given by $$\min_{T} P_1(t, T) = \min_{T} \int_{-T_0}^{T_0} w(\tau)\{|s(\tau + t + T_S) - s(\tau + t + T + T_S)|^n\}d\tau, \tag{1}$$

where $s(t)$ is time-series data of radar signal at the position, $T$ is the time difference, $2T0$ is the window width for the calculation of differential signals, $Ts$ is a time shift parameter, $w(\tau)$ is a window function, and $n>0$. For example, the time difference $T$ which minimizes the intensity of differential signal $P1(t,T)$ is equivalent to the respiratory interval or heartbeat interval. In one example, $s(t)$ is a complex signal comprising of in-phase and quadrature components. $s(t)$ may be real signal or real part of the complex signal comprising of in-phase and quadrature components. Window function $w(\tau)$ includes rectangular window, B-spline window, Hann window, Hamming window, and Tukey window. In one example, $Ts$ is a constant or $-T/2$. Also, in one example, $n=2$. Another example of the minimization of the intensity of the differential signals at a position is given by $$\min_{T} P_2(t, T) = \tag{2}$$

$$\min_{T} \int_{-T_0}^{T_0} w(\tau)\{|s(\tau + t) - s(\tau + t - T)|^n + |s(\tau + t) - s(\tau + t + T)|^n\}d\tau.$$

For the respiratory interval estimation the time difference $T$ may be minimized within the possible range of respiratory interval. The controller comprising circuitry of the present vital information acquisition apparatus may be configured to estimate respiratory intervals of the subject by the time difference which minimize the intensity of the differential signals at each position within the time difference from 0.2 to 10 s.

For the heartbeat interval estimation the time difference $T$ may be minimized within the possible range of heartbeat interval. The controller comprising circuitry of the present vital information acquisition apparatus may be configured to estimate heartbeat intervals of the subject by the time difference which minimize the intensity of the differential signals at each position within the time difference from 0.1 to 2 s.

For example, in order to estimate respiratory intervals, heartbeat interval and/or position of a subject, the time difference $T$ may be minimized within the possible range of respiratory interval and/or heartbeat interval of the subject. The controller comprising circuitry of the present vital information acquisition apparatus may be configured to be input subject information, and cause the range of time difference for the minimization of the intensity of the differential signals to the possible range of respiratory interval and/or heartbeat interval of the subject.

The controller comprising circuitry of the present vital information acquisition apparatus may apply at least one smoothing filter including median filter, moving average filter and Hampel filter to the intensity of the differential signals at each position in the time domain and/or in the spatial domain, to respiratory intervals and/or heartbeat intervals of the subject. For example, the controller comprising circuitry of the present vital information acquisition apparatus may apply at least one smoothing filter including median filter, moving average filter and Hampel filter to respiratory intervals and/or heartbeat intervals of the subject. One example of the application of a smoothing filter to the intensity of the differential signal in the time domain is given by $$\min_{T} F[P_2(t, T)] = \qquad (3)$$

$$\min_{T} F\left[\int_{-T_0}^{T_0} w(\tau)\{|s(\tau + t) - s(\tau + t - T)|^n + |s(\tau + t) - s(\tau + t + T)|^n\}d\tau\right],$$

where F[ ] is a smoothing filter with respect to t and/or T.

The controller comprising circuitry of the present vital information acquisition apparatus may determine the subject is at a certain position when a large drop of the intensity of differential signal, respiratory interval, and/or heartbeat interval are detected at the position.

The radar system of the present vital information acquisition apparatus may include a plurality of transmitting antennas and/or a plurality of receiving antennas and be configured to transmit a plurality of electromagnetic waves to a plurality of directions and/or receive a plurality of received electromagnetic waves reflected from a plurality of directions; and the controller comprising circuitry of the present vital information acquisition apparatus may be configured to estimate respiratory intervals, heartbeat intervals, and/or the position of at least one subject among a plurality of directions.

The vital information acquisition apparatus of an embodiment of the present invention may further comprise a driving unit connected to the radar system. A controller comprising circuitry of the present vital information acquisition apparatus may be configured to direct the transmitting antenna and receiving antenna to the measurement direction, and to estimate respiratory intervals, heartbeat intervals, and/or the position of at least one subject among a plurality of directions.

The vital information acquisition apparatus of an embodiment of the present invention may further comprise a plurality of radar systems which include at least one transmitting antenna and at least one receiving antenna and are configured to transmit a plurality of electromagnetic waves to a plurality of positions and receive a plurality of electromagnetic waves reflected from a plurality of positions. A controller comprising circuitry of the vital information acquisition apparatus may be configured to synchronize the radar systems, employ a frequency-division multiple access technique or code division multiple access, and cause to estimate respiratory intervals, heartbeat intervals and/or positions of a plurality of subjects without interference.

The controller comprising circuitry of the present vital information acquisition apparatus may be configured to calculate variation of radar signals at each position in the time domain, and determine the existence of breathing of the subject and/or the existence of a subject at the position using the variation of radar signals and/or the intensity of radar signals. One example of the variation of radar signal is given by $$V(t)=s(t)-s(t+\Delta t)^n, \qquad (4)$$

where $\Delta t$ is a certain time, n>0. In one example, n=2. For example, $\Delta t$ is equivalent to sampling interval in the time domain. At may be within the range of 0.001 to 0.2 s for vital information acquisition. A smoothing filter may be applied to the variation of radar signals.

The controller comprising circuitry of the present vital information acquisition apparatus may be configured to determine that the subject is in apnea or hypopnea when variation of radar signals decreases and/or when variation of the intensity of the differential signals in the time domain decreases.

The controller comprising circuitry of the present vital information acquisition apparatus may be configured to determine that the subject is recovered from apnea or hypopnea when variation of radar signals increases and/or when variation of the intensity of the differential signals in the time domain increases.

The controller comprising circuitry of the present vital information acquisition apparatus may be configured to transmit vital information to remote server. The vital information acquisition apparatus of an embodiment of the present invention may further comprise at least one vital information transmission device comprising circuitry which transmits vital information to a remote server including a remote data storage device in a cloud computing environment.

Figure 4:
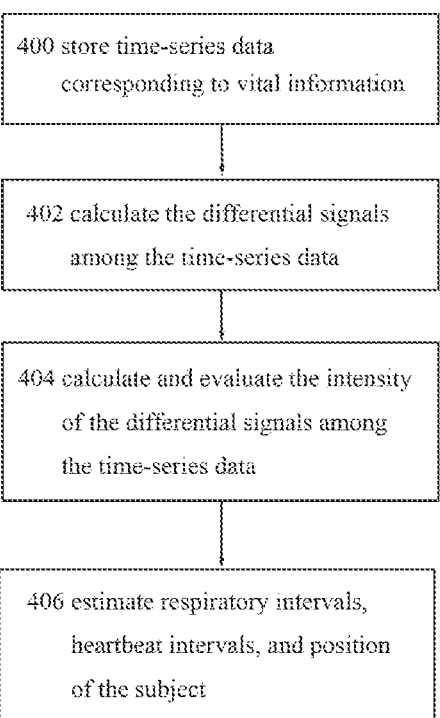
FIG. 4 is a schematic diagram of a vital information acquisition method that estimates respiratory interval of a subject by the time difference which minimizes the intensity of the differential signals.

Vital information acquisition method of an embodiment of the present invention stores time-series data corresponding to vital information, calculates the differential signals, evaluates the differential signal intensity, and estimates respiratory intervals, heartbeat intervals, and/or position of a subject. FIG. 4 shows a schematic diagram of a vital information acquisition method that estimates respiratory interval of a subject by the time difference which minimizes the intensity of the differential signals. The vital information acquisition method of an embodiment of the present invention stores time-series data corresponding to vital information 400, calculates the differential signals among the time-series data 402, calculates and evaluates the intensity of the differential signals among the time-series data 404, and estimates respiratory intervals, heartbeat intervals, and position of the subject 406.

The vital information acquisition method of an embodiment of the present invention may estimate respiratory intervals, heartbeat intervals, and/or position of the subject by the time difference which minimizes the intensity of the differential signals.

Figure 5:
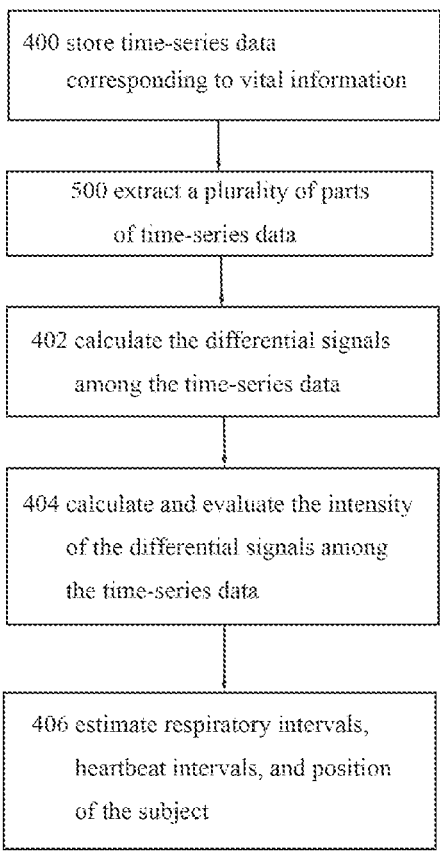
FIG. 5 is a schematic diagram of a vital information acquisition method that extracts a plurality of parts of the time-series data using one of window functions, including rectangular window, B-spline window, Hann window, Hamming window, and Tukey window for the calculation of differential signals.

The vital information acquisition method of an embodiment of the present invention may extract a plurality of parts of the time-series data using one of window functions, including rectangular window, B-spline window, Hann window, Hamming window, and Tukey window. FIG. 5 shows a schematic diagram of a vital information acquisition method that extracts a plurality of parts of the time-series data using one of window functions, including rectangular window, B-spline window, Hann window, Hamming window, and Tukey window for the calculation of differential signals. The vital information acquisition method of an embodiment of the present invention stores time-series data corresponding to vital information 400, extracts a plurality of parts of the time-series data corresponding to vital information 500, calculates the differential signals among the time-series data 402, calculates and evaluates the intensity of the differential signals among the time-series data 404, and estimates respiratory intervals, heartbeat intervals, and position of the subject 406.

The vital information acquisition method of an embodiment of the present invention may calculate variation of time-series data corresponding to vital information, and determine the existence of breathing of the subject and/or the existence of a subject using the variation and/or intensity of time-series data corresponding to vital information.

The vital information acquisition method of an embodiment of the present invention may apply at least one smoothing filter including median filter, moving average filter and Hampel filter to the intensity of the differential signals at each position, respiratory interval of the subject, variation of time-series data corresponding to vital information, intensity of time-series data corresponding to vital information, and/or heartbeat interval of the subject in the time domain and/or in the spatial domain.

Figure 6:
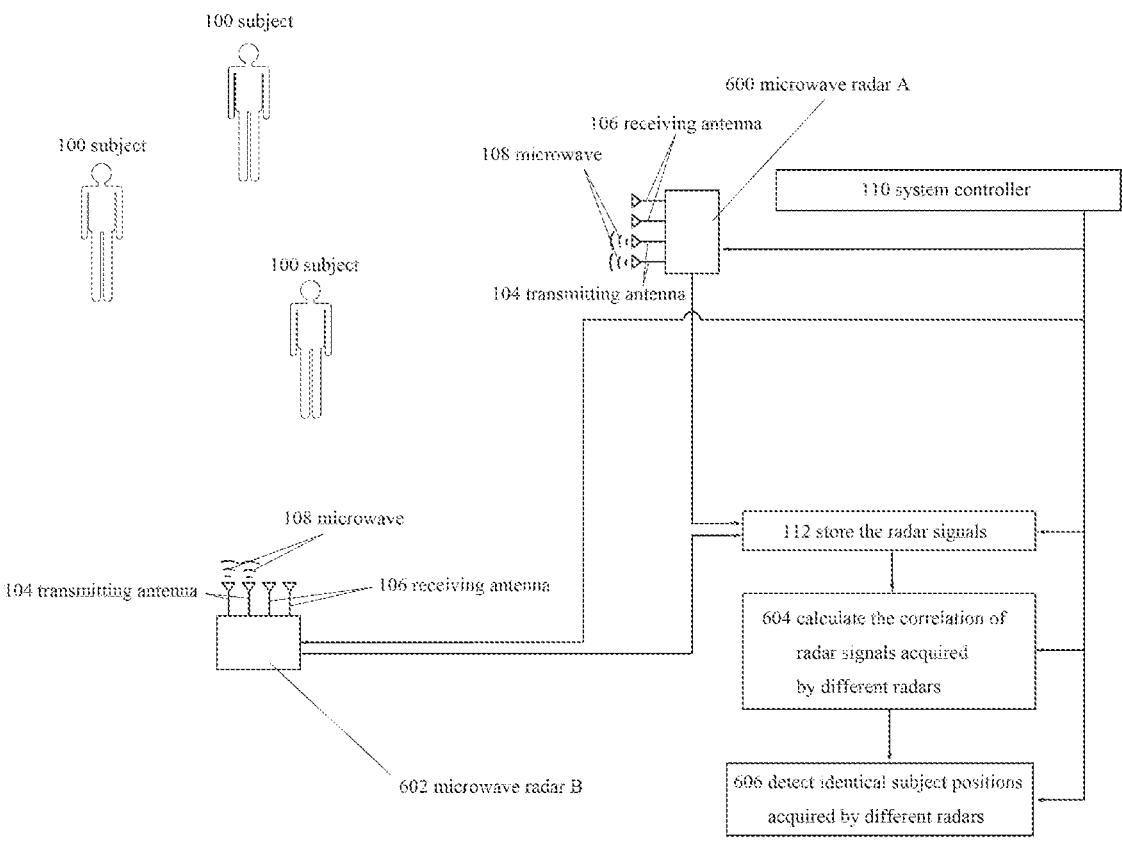
FIG. 6 is a schematic diagram of a vital information acquisition apparatus that transmits microwaves to plural subjects and estimates vital information of plural subjects using signal correlation between the radar signals acquired by different radars.

Vital information acquisition apparatus of an embodiment of the present invention transmits microwaves to plural subjects and estimates vital information of plural subjects using signal correlation between the radar signals acquired by different radars. FIG. 6 shows a schematic diagram of a vital information acquisition apparatus that transmits microwaves to plural subjects and estimates vital information of plural subjects using signal correlation between the radar signals acquired by different radars. A vital information acquisition apparatus includes at least two microwave radars. A microwave radar 600 includes at least one transmitting antenna 104 and at least one receiving antenna 106. Microwaves 108 are transmitted from transmitting antennas 104. Transmitted microwave 108 can be modulated using one of pulse compression techniques, e.g. m-sequence. Transmitted microwaves are reflected at the body surfaces of the subjects 100.

Reflected microwaves are received by receiving antennas 106. A system controller 110 comprising circuitry configured to convert a plurality of received microwaves to a plurality of radar signals, store the radar signals 112, calculate the correlation of radar signals acquired by different radars 604, and detect identical subject positions acquired by different radars 606.

Figure 7:
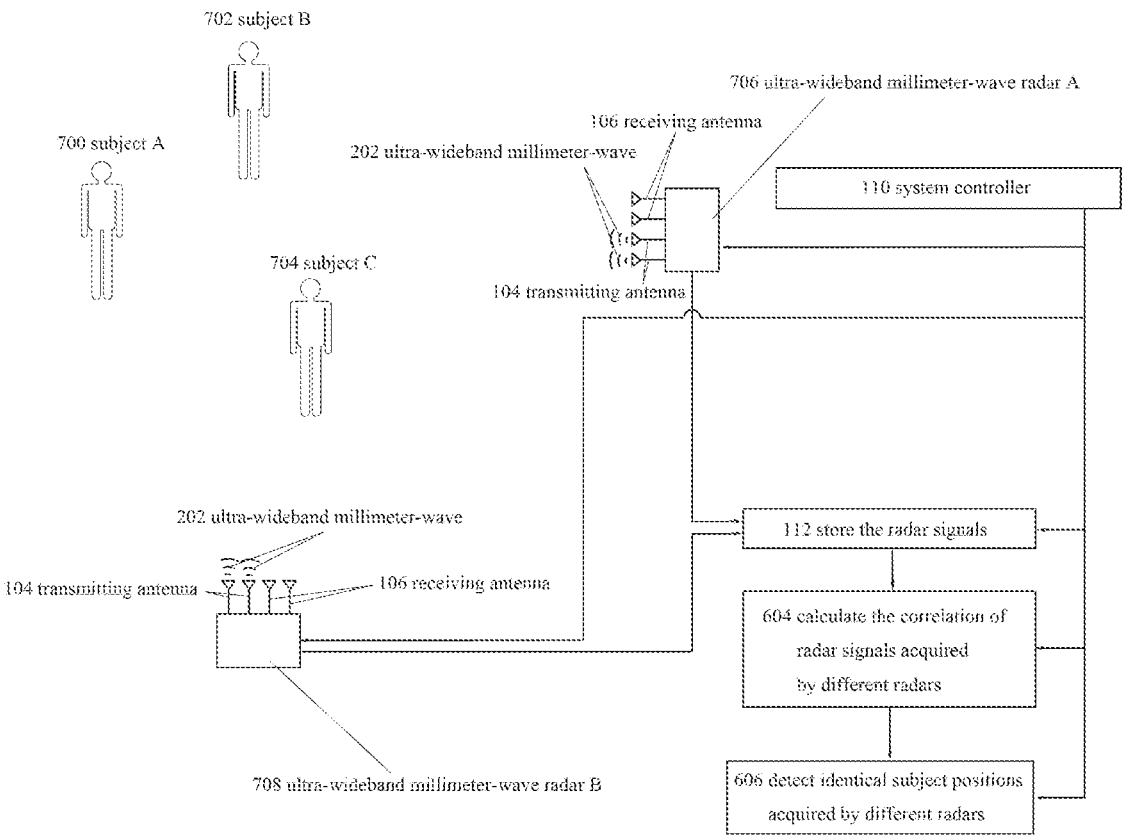
FIG. 7 is a schematic diagram of a vital information acquisition apparatus with plural ultra-wideband millimeter-wave radars that transmits ultra-wideband millimeter-waves to plural subjects, estimates vital information of plural subjects using signal correlation between the radar signals acquired by different radars.

Ultra-wideband millimeter-wave radars can be used. FIG. 7 shows a schematic diagram of a vital information acquisition apparatus that transmits ultra-wideband millimeter-waves to plural subjects and estimates vital information of plural subjects using signal correlation between the radar signals acquired by different radars. A vital information acquisition apparatus includes at least two ultra-wideband millimeter-wave radars 706 and 708. An ultra-wideband millimeter-wave radar includes at least one transmitting antenna 104 and at least one receiving antenna 106. Ultra-wideband millimeter-waves 202 are transmitted from transmitting antennas 104. Transmitted ultra-wideband millimeter-wave 202 can be modulated using one of pulse compression techniques, e.g. m-sequence. Transmitted ultra-wideband millimeter-waves are reflected at the body surfaces of plural subjects 700, 702 and 704. Reflected ultra-wideband millimeter-waves are received by receiving antennas 106. A system controller 110 comprising circuitry configured to convert a plurality of received ultra-wideband millimeter-waves 202 to a plurality of radar signals, store the radar signals 112, calculate the correlation of radar signals acquired by different radars 604, and detect identical subject positions acquired by different radars 606.

A virtual array radar may be synthesized from an ultra-wideband millimeter-wave radar with plural transmitting antennas and plural receiving antennas when the target distance is sufficiently longer than the array size of the radar and the mutual coupling between antennas is negligible. The controller comprising circuitry of a vital information acquisition apparatus may be configured to synthesize a virtual array radar from each ultra-wideband millimeter-wave radar with plural transmitting antennas and plural receiving antennas. When an ultra-wideband millimeter-wave radar has three transmitting antennas and four receiving antennas, a virtual array radar with a total of 12 channels can be synthesized.

A vital information acquisition apparatus may construct complex radar image data using one of beamforming techniques. When a vital information acquisition apparatus employs FMCW ultra-wideband millimeter-wave radars, the complex radar image data can be acquired by Fourier transform application in the fast-time direction and Fourier transform application in the channel number domain of the virtual array.

The controller comprising circuitry of a vital information acquisition apparatus according may further be configured to subtract the DC component of radar image data in order to suppress the contribution of static clutters. The DC component of complex radar image data includes time average of radar image data as follows:

$$I_c(t, r, \theta) = I_0(t, r, \theta) - \frac{1}{T} \int_{t-T_c}^{\tau} I_0(\tau, r, \theta) d\tau, \tag{5}$$

where t is measurement time, that is slow-time, r is measurement range, $\theta$ is measurement angle, $T_c$ is averaging time for static clutter suppression, and $I_c(t, r, \theta)$ and $I_0(t, r, \theta)$ are complex radar image data before and after static clutter suppression, respectively.

The controller comprising circuitry of a vital information acquisition apparatus may further be configured to detect plural human and/or animal target candidates and estimate their positions using radar image data. For the detection of the above candidates, we may use the power of the complex radar image data given by:

$$I_P(t, r, \theta) = \frac{1}{T_P} \int_{t-T_c}^{\tau} |I_0(\tau, r, \theta)|^2 d\tau, \tag{6}$$

where $T_P$ is averaging time for intensity estimation.

The controller comprising circuitry of a vital information acquisition apparatus may further be configured to construct respiratory image data from radar image data in order to detect plural human and/or animal targets and their positions. The respiratory image data construction includes the band-path filter application to real radar image data, and band-path filter application to phase information of complex radar image data. An example of respiratory image data $\tau_r(t, r, \theta)$, acquired by a band-path filter application to phase information of complex radar image data, is given by:

$$\tau_r(t, r, \theta) = \operatorname*{argmin}_{\tau} f_{t,r,\theta}(\tau), \tag{7}$$

$$f_{t,r,\theta}(\tau) = \frac{1}{2T_0} \int_{t-2T_1}^{\tau} |d(t', r, \theta) - (d(t'\tau, r, \theta)|^2 dt' + \tag{8}$$

-continued $$\frac{1}{2T_0} \int_{t-2T_0}^{\tau} |d(t', r, \theta) - (d(t' - \tau, r, \theta)|^2 dt'$$

$$d(t, r, \theta) = [d_0(t, r, \theta) - d_0(t, r, \theta) \approx h_{HPF}(t) \approx h_{LPF}(t), \qquad (9)$$

$$d_0(t, r, \theta) = \frac{\lambda}{4\pi} \angle I_o(t, r, \theta), \qquad (10)$$

where $\lambda$ is the center wavelength of a ultra-wideband millimeter-wave employed by the radars, $\angle I_c(t, r, \theta)$ is the phase angle of complex radar image data $I_c(t, r, \theta)$, and $h_{HPF}(t)$ and $h_{LPF}(t)$ are a high-pass filter and a low-pass filter, respectively.

The controller comprising circuitry of a vital information acquisition apparatus may further be configured to construct respiratory interval radar image data, where the respiratory interval radar image data includes respiratory interval information at all or part of the coordinates of radar image data. We may calculate the respiratory rate of the coordinates with high power, that is calculate the respiratory rate under the condition of $I_P(t, r, \theta) > I_{thre}$ in order to reduce computational load.

The controller comprising circuitry of a vital information acquisition apparatus may further be configured to detect plural human and/or animal targets and estimate their positions using one of clustering techniques, where the clustering techniques include X-means algorithm, k-means algorithm.

The controller comprising circuitry of a vital information acquisition apparatus may be configured to apply one of clustering techniques to the respiratory interval radar image data acquired by each ultra-wideband millimeter-wave radar individually, and synthesize the clusters acquired by each respiratory interval radar image data.

The controller comprising circuitry of a vital information acquisition apparatus may be configured to calculate the correlation between respiratory interval information at all clusters acquired by different radars. An example of the correlation between respiratory interval information is given by:

$$\rho_{k,i,l,j} = \frac{\int \left(u_{k,i}(t) - \overline{u_{k,i}(t)}\right)\left(u_{l,j}(t) - \overline{u_{l,j}(t)}\right)dt}{\sqrt{\int \left(u_{k,i}(t) - \overline{u_{k,i}(t)}\right)^2 dt \int \left(u_{l,j}(t) - \overline{u_{l,j}(t)}\right)^2 dt}}, \qquad (11)$$

where $u_{k,j}(t)$ is the respiratory interval information of i-th cluster in the radar image data acquired by k-th radar, $u_{l,j}(t)$ is the respiratory interval information of j-th cluster in the radar image data acquired by l-th radar, and $\overline{u_{k,j}(t)}$ and $\overline{u_{l,j}(t)}$ are respectively the time average of $u_{k,j}(t)$ and $u_{l,j}(t)$. This process may be used to detect identical subject positions acquired by different radars because high cross-correlation value given by Equation (11) indicates that i-th cluster and j-th cluster are the identical subject.

Figure 8:
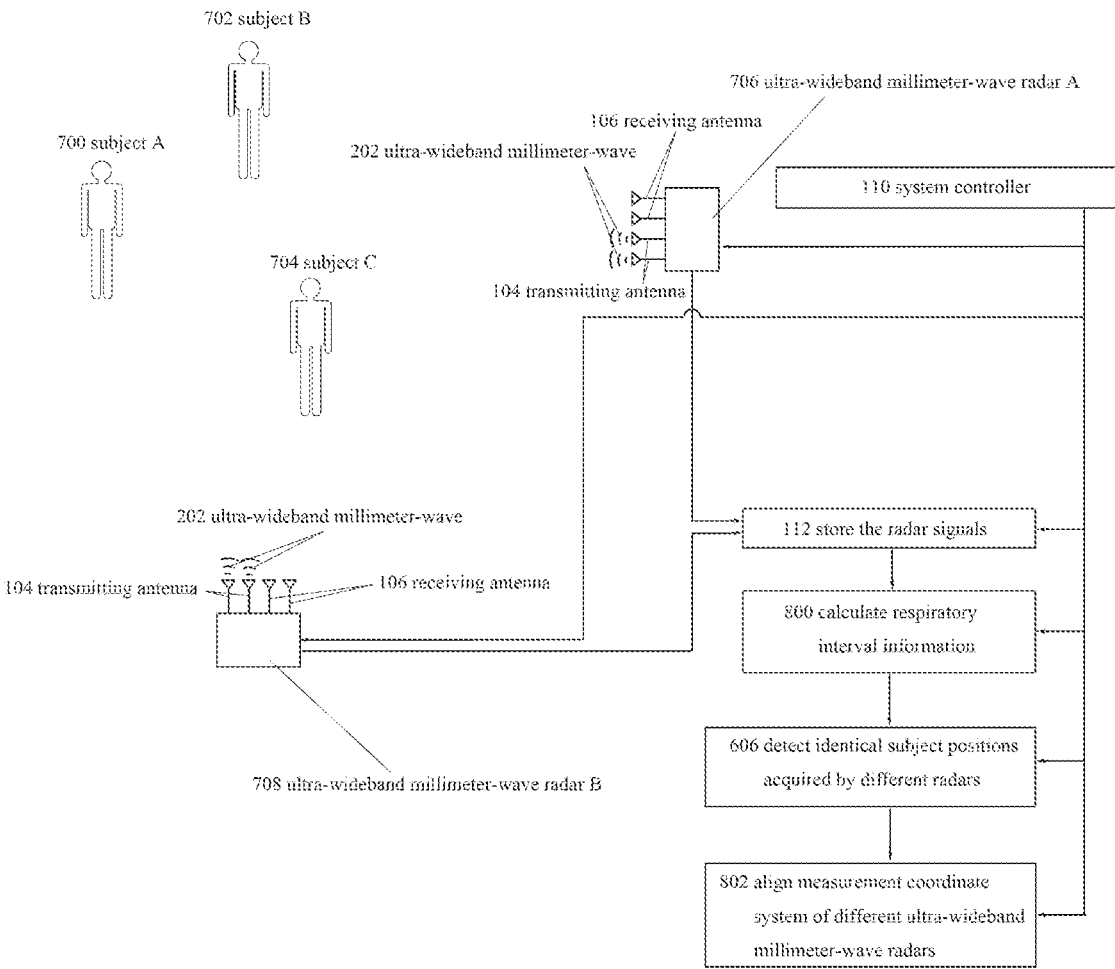
FIG. 8 is a schematic diagram of a vital information acquisition apparatus with plural ultra-wideband millimeter-wave radars that transmits ultra-wideband millimeter-waves to plural subjects, estimates vital information of plural subjects and aligns measurement coordinates of plural radars using signal correlation between the radar signals acquired by different radars.

The controller comprising circuitry of a vital information acquisition apparatus may be configured to align the coordinates systems of different radars using at least two cluster pairs of different radars with highest correlation values of respiratory interval information. The cluster pair of different radars with high correlation value of respiratory interval information, for example given by Equation (11), indicates that the two clusters are acquired by the identical subject. An example of the alignment process using two cluster pairs of different radars is Procrustes analysis. FIG. 8 shows a schematic diagram of a vital information acquisition apparatus that aligns coordinate systems of different ultra-wideband millimeter-wave radars. A vital information acquisition apparatus includes at least two ultra-wideband millimeter-wave radars 706 and 708. An ultra-wideband millimeter-wave radar includes at least one transmitting antenna 104 and at least one receiving antenna 106. Ultra-wideband millimeter-waves 202 are transmitted from transmitting antennas 104. Transmitted ultra-wideband millimeter-wave 202 can be modulated using one of pulse compression techniques, e.g. m-sequence. Transmitted ultra-wideband millimeter-waves are reflected at the body surfaces of plural subjects 700, 702 and 704. Reflected ultra-wideband millimeter-waves are received by receiving antennas 106. A system controller 110 comprising circuitry configured to convert a plurality of received ultra-wideband millimeter-waves 202 to a plurality of radar signals, store the radar signals 112, calculate respiratory interval information 800, detect identical subject positions acquired by different radars 606, and align measurement coordinate system of different ultra-wideband millimeter-wave radars 802.

Figure 9:
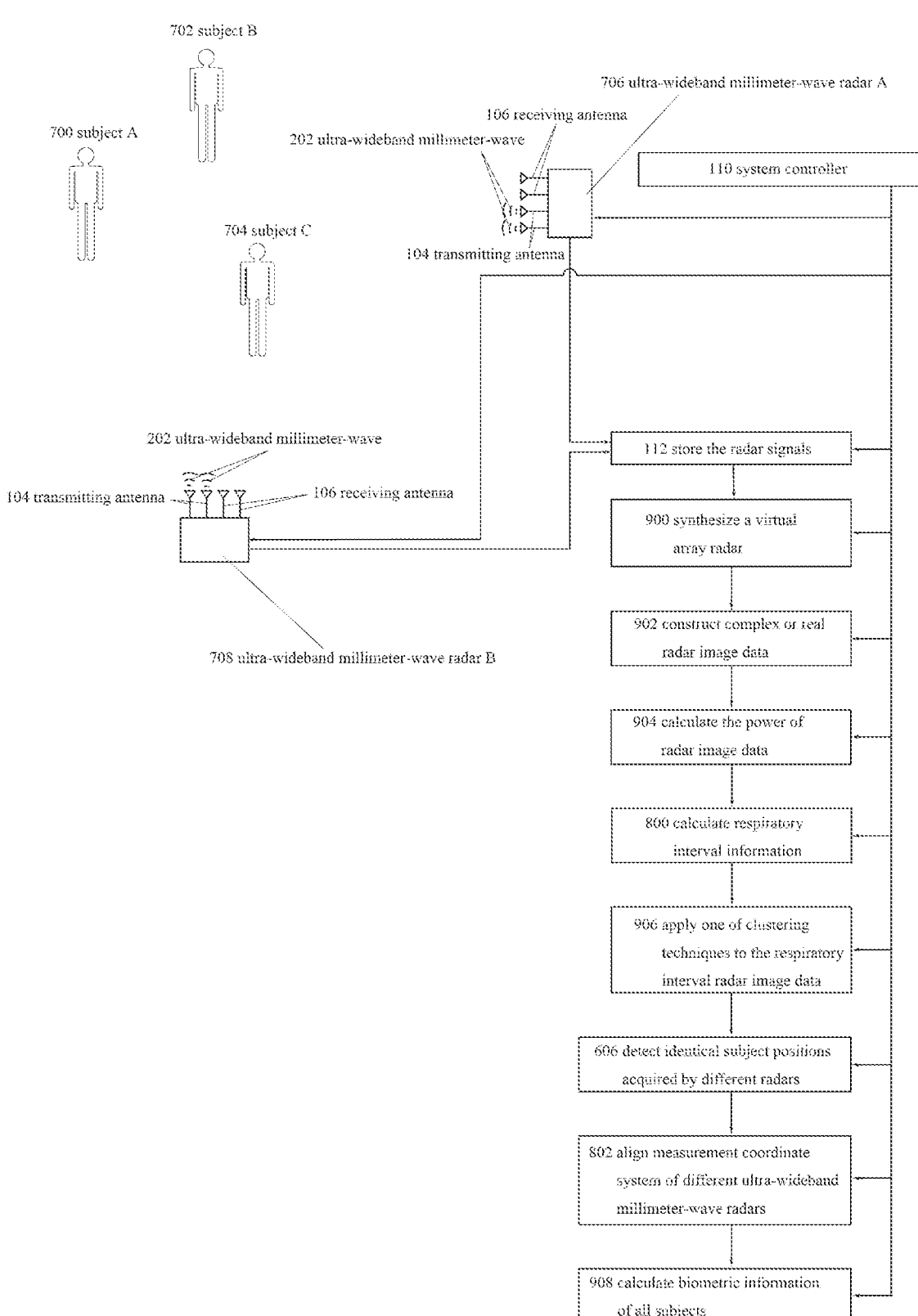
FIG. 9 is a schematic diagram of a vital information acquisition apparatus that aligns coordinate systems of different ultra-wideband millimeter-wave radars and calculates biometric information.

The controller comprising circuitry of a vital information acquisition apparatus may be configured to align the coordinates systems of different radars using two cluster pairs of different radars with highest correlation values of respiratory interval information, and align the coordinates systems of different radars using all cluster pairs of different radars, where the alignment information acquired by two cluster pairs of different radars with highest correlation values of respiratory interval information is employed as the initial value for the alignment procedure using all cluster pairs of different radars. FIG. 9 shows a schematic diagram of a vital information acquisition apparatus that aligns coordinate systems of different ultra-wideband millimeter-wave radars and calculates biometric information. A vital information acquisition apparatus includes at least two ultra-wideband millimeter-wave radars 706 and 708. An ultra-wideband millimeter-wave radar includes at least one transmitting antenna 104 and at least one receiving antenna 106. Ultra-wideband millimeter-waves 202 are transmitted from transmitting antennas 104. Transmitted ultra-wideband millimeter-wave 202 can be modulated using one of pulse compression techniques, e.g. m-sequence. Transmitted ultra-wideband millimeter-waves are reflected at the body surfaces of plural subjects 700, 702 and 704. Reflected ultra-wideband millimeter-waves are received by receiving antennas 106. A system controller 110 comprising circuitry configured to convert a plurality of received ultra-wideband millimeter-waves 202 to a plurality of radar signals, store the radar signals 112, synthesize a virtual array radar from each ultra-wideband millimeter-wave radar with plural transmitting antennas and plural receiving antennas 900, construct complex or real radar image data using one of beamforming techniques 902, calculate the power of radar image data 904, calculate respiratory interval information 800, apply one of clustering techniques to the respiratory interval radar image data 906, detect identical subject positions acquired by different radars 606, and align measurement coordinate system of different ultra-wideband millimeter-wave radars 802, and calculate biometric information of all subjects 908.

The controller comprising circuitry of a vital information acquisition apparatus may be configured to eliminate the cluster pair of different radars when the positions measured by different radars are distant.

Figure 10:
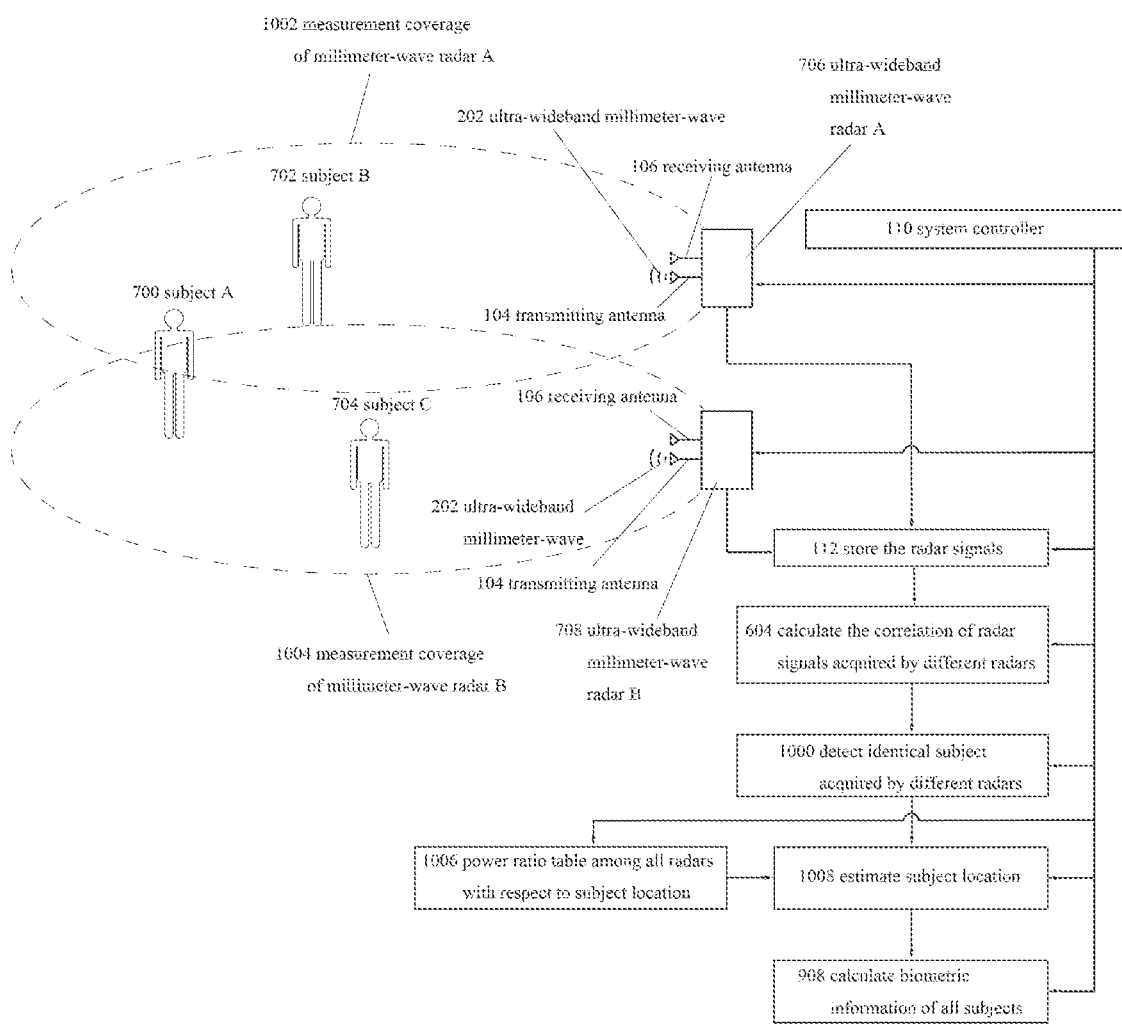
FIG. 10 is a schematic diagram of a vital information acquisition apparatus, where the measurement coverages of different ultra-wideband millimeter-wave radars partially overlap.

Measurement coverages of different ultra-wideband millimeter-wave radars may partially overlap. FIG. 10 shows a schematic diagram of a vital information acquisition apparatus, where the measurement coverages of different ultra-wideband millimeter-wave radars partially overlap. A vital information acquisition apparatus includes at least two ultra-wideband millimeter-wave radars 706 and 708. An ultra-wideband millimeter-wave radar includes at least one transmitting antenna 104 and at least one receiving antenna 106. Ultra-wideband millimeter-waves 202 are transmitted from transmitting antennas 104. Transmitted ultra-wideband millimeter-wave 202 can be modulated using one of pulse compression techniques, e.g. m-sequence. Transmitted ultra-wideband millimeter-waves are reflected at the body surfaces of plural subjects 700, 702 and 704. Reflected ultra-wideband millimeter-waves are received by receiving antennas 106. A system controller 110 comprising circuitry configured to convert a plurality of received ultra-wideband millimeter-waves 202 to a plurality of radar signals, store the radar signals 112, calculate the correlation of radar signals acquired by different radars 604, detect identical subject acquired by different radars 1000, estimate subject location 1008, and calculate biometric information 908. An example of subject location estimation is the employment of power ratio table among all radars with respect to subject location 1006. In the case of FIG. 10, the signal power of subject A 700 is received by both radar A and radar B. The signal power of subject B 702 received by radar A 706 is much larger than that received by radar B 708, and the signal power of subject C 704 received by radar A 706 is much smaller than that received by radar B 708. The apparatus of an embodiment of the present invention detects the identical subjects acquired by different radars 606, and estimates their locations using a power ratio table among all radars with respect to subject location 1006.

At least one ultra-wideband millimeter-wave radar of a vital information acquisition apparatus may transmit and receive a plurality of ultra-wideband millimeter-waves with the sampling rate of 20 ms or less in order to measure the heart beat interval, where in general the heart beat interval is from 0.5 to 1 s.

At least one ultra-wideband millimeter-wave radar of a vital information acquisition apparatus may transmit and receive a plurality of ultra-wideband millimeter-waves with the sampling rate of from 1 to 20 ms in order to measure the heart beat interval, where in general the heart beat interval is from 0.5 to 1 s.

A vital information acquisition method of an embodiment of the present invention stores the radar signals, calculates the correlation between the radar signals acquired by different radars, and detects identical subject positions acquired by different radars.

A vital information acquisition method of an embodiment of the present invention stores the radar signals, calculates respiratory interval information, detects identical subject positions acquired by different radars, and aligns measurement coordinate system of different ultra-wideband millimeter-wave radars.

A vital information acquisition method of an embodiment of the present invention stores the radar signals, calculates the correlation between the radar signals acquired by different radars, and detects identical subject positions acquired by different radars, estimates subject location, and calculate biometric information, where the estimation of subject location includes the employment of power ratio table among all radars with respect to subject location.

Figure 11:
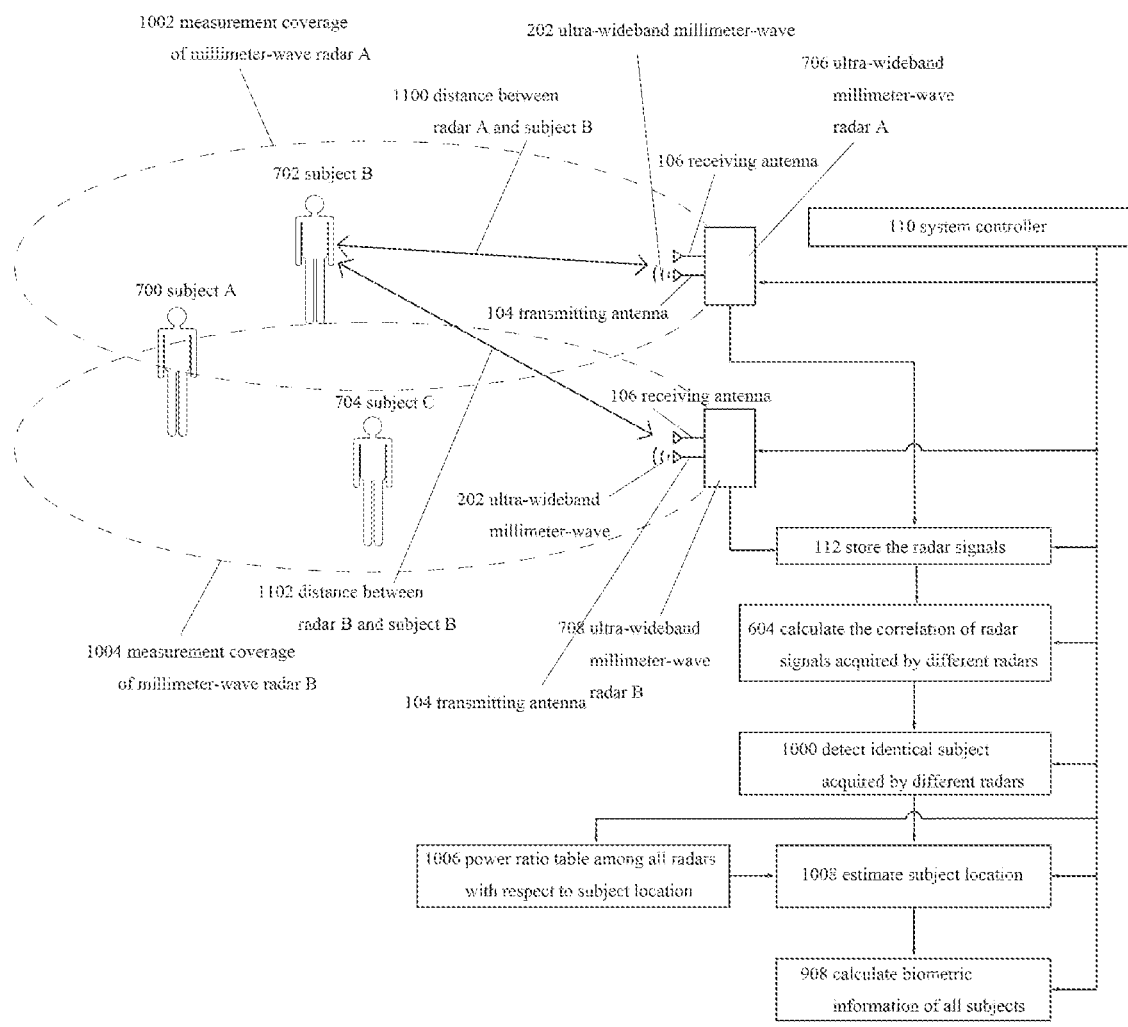
FIG. 11 is a schematic diagram of a vital information acquisition apparatus that transmits ultra-wideband millimeter-waves to plural subjects and estimates vital information of plural subjects.

Vital information acquisition apparatus of an embodiment of the present invention transmits ultra-wideband millimeter-waves to plural subjects and estimates vital information of plural subjects using signal correlation between the radar signals acquired by different radars. FIG. 11 shows a schematic diagram of a vital information acquisition apparatus that transmits ultra-wideband millimeter-waves to plural subjects and estimates vital information of plural subjects. A vital information acquisition apparatus includes at least two ultra-wideband millimeter-wave radars 706 and 708. An ultra-wideband millimeter-wave radar includes at least one transmitting antenna 104 and at least one receiving antenna 106. Ultra-wideband millimeter-waves 202 are transmitted from transmitting antennas 104. Transmitted ultra-wideband millimeter-wave 202 can be modulated using one of pulse compression techniques, e.g. m-sequence. Transmitted ultra-wideband millimeter-waves are reflected at the body surfaces of plural subjects 700, 702 and 704. Reflected ultra-wideband millimeter-waves are received by receiving antennas 106. A system controller 110 comprising circuitry configured to convert a plurality of received ultra-wideband millimeter-waves 202 to a plurality of radar signals, store the radar signals 112, calculate the correlation of radar signals acquired by different radars 604, detect identical subject acquired by different radars 1000, estimate subject location 1008, and calculate biometric information 908. An example of subject location estimation is the employment of power ratio table among all or a part of radars with respect to subject location 1006. Other example of subject location estimation is the employment of triangulation using distance information of all or a part of radars. Distance information may be calculated from time-of-flight information between each subject and each radar. In the case of FIG. 11, the signal power of subject A 700 is received by both radar A and radar B. The signal power of subject B 702 received by radar A 706 is much larger than that received by radar B 708, and the signal power of subject C 704 received by radar A 706 is much smaller than that received by radar B 708. The apparatus of an embodiment of the present invention detects the identical subjects acquired by different radars 1000, and estimates their locations using a power ratio table among all radars with respect to subject location 1006. The location of subject also may be calculated by the employment of the triangulation using distance information from at least two radars. For example, the two-dimensional location of subject B can be located by the employment of triangulation using the distance between radar A and subject B 1100 and the distance between radar B and subject B 1102. The three-dimensional location of each subject requires at least three radars by the employment of triangulation. The distance between each subject and each radar may be calculated by time-of-flight information. The triangulation, sometimes called 3D TOF (time-of-flight) is useful when the distance between radars is sufficiently longer than the measurement accuracy in distance between each subject and each radar.

Figure 12:
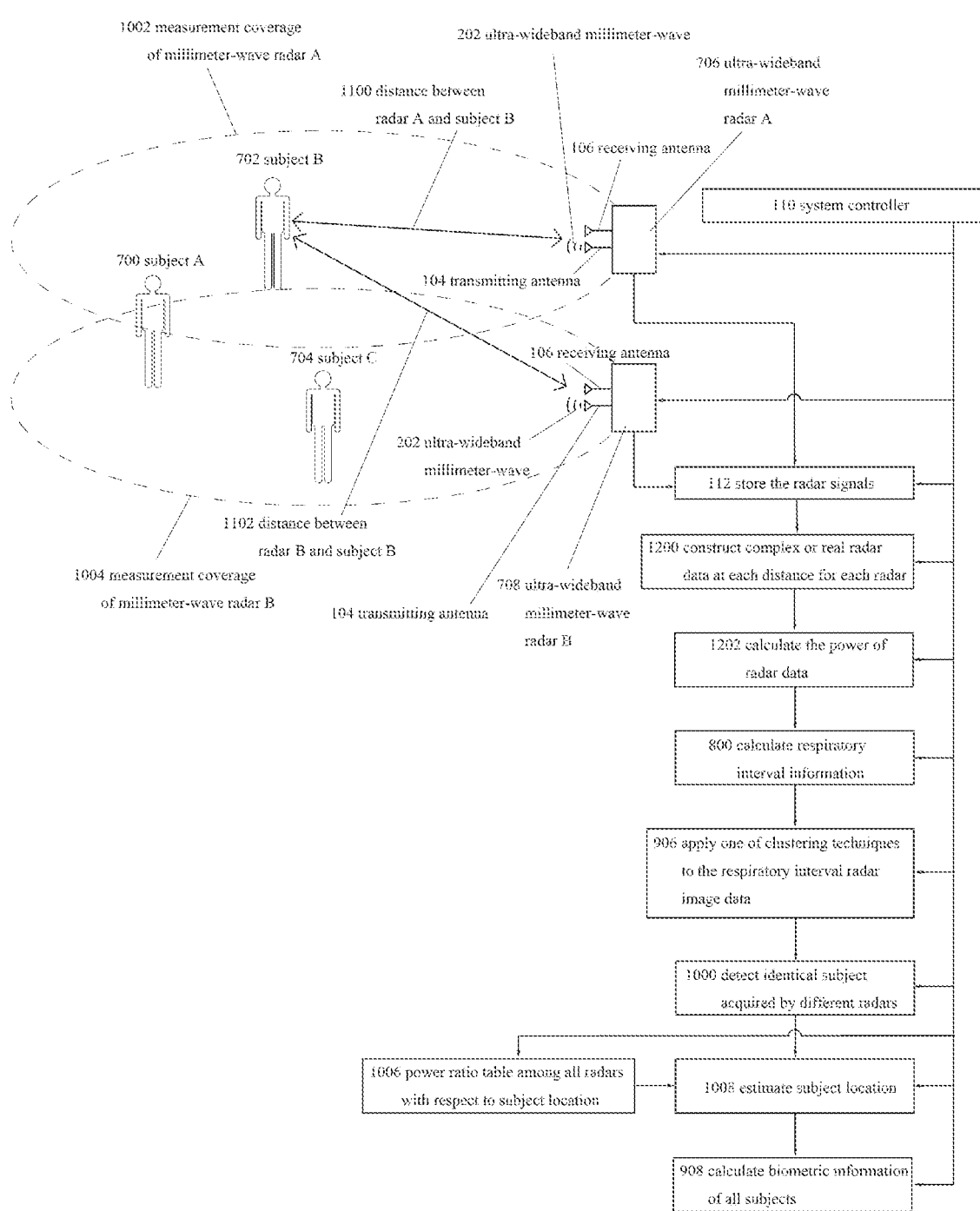
FIG. 12 is a schematic diagram of a vital information acquisition apparatus that aligns coordinate systems of different ultra-wideband millimeter-wave radars and calculates biometric information.

A vital information acquisition apparatus of an embodiment of the present invention may be comprising: at least two ultra-wideband millimeter-wave radars each of which includes at least one transmitting antenna and at least one receiving antenna and is configured to transmit a plurality of ultra-wideband millimeter-waves to plural subjects and receive a plurality of ultra-wideband millimeter-waves reflected by the subjects; and a controller comprising circuitry configured to convert a plurality of received ultra-wideband millimeter-waves to a plurality of radar signals, store the radar signals, construct radar data at each distance, calculate the power of radar data, estimate respiratory information, apply one of clustering techniques to the respiratory interval radar data, detect identical subject acquired by different radars, estimate subject location, and calculate biometric information, the respiratory information estimation includes the band-path filter application to real radar data, and band-path filter application to phase information of complex radar image data, the respiratory interval radar data includes respiratory interval information at all or part of the distances of radar image data, and the clustering techniques include X-means algorithm, k-means algorithm. FIG. 12 shows a schematic diagram of a vital information acquisition apparatus that aligns coordinate systems of different ultra-wideband millimeter-wave radars and calculates biometric information. A vital information acquisition apparatus includes at least two ultra-wideband millimeter-wave radars 706 and 708. An ultra-wideband millimeter-wave radar includes at least one transmitting antenna 104 and at least one receiving antenna 106. Ultra-wideband millimeter-waves 202 are transmitted from transmitting antennas 104. Transmitted ultra-wideband millimeter-wave 202 can be modulated using one of pulse compression techniques, e.g. m-sequence. Transmitted ultra-wideband millimeter-waves are reflected at the body surfaces of plural subjects 700, 702 and 704. Reflected ultra-wideband millimeter-waves are received by receiving antennas 106. A system controller 110 comprising circuitry configured to convert a plurality of received ultra-wideband millimeter-waves 202 to a plurality of radar signals, store the radar signals 112, construct complex or real radar data at each distance for each radar 1200, calculate the power of radar data 1202, calculate respiratory interval information 800, apply one of clustering techniques to the respiratory interval radar data 906, detect identical subjects acquired by different radars 1000, estimate subject location 1008, and calculate biometric information 908. An example of subject location estimation is the employment of power ratio table among all radars with respect to subject location 1006. In the case of FIG. 12, the signal power of subject A 700 is received by both radar A and radar B. The signal power of subject B 702 received by radar A 706 is much larger than that received by radar B 708, and the signal power of subject C 704 received by radar A 706 is much smaller than that received by radar B 708. The apparatus of an embodiment of the present invention detects the identical subjects acquired by different radars 606, and estimates their locations using a power ratio table among all radars with respect to subject location 1006. Other example of subject location estimation is the employment of triangulation using distance information of all or a part of radars. Distance information may be calculated from time-of-flight information between each subject and each radar.

The synchronization accuracy of a vital information acquisition apparatus the between radars may be 1ns or worse, because the apparatus of an embodiment of the present invention does not employ beamforming that requires accurate phase synchronization.

Figure 13:
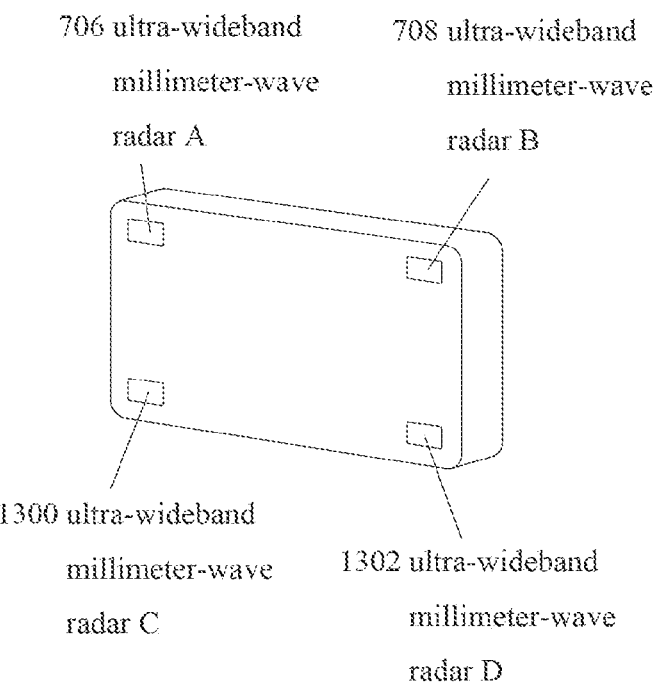
FIG. 13 is a schematic view of a vital information acquisition apparatus that employs four radars located at four corners of the apparatus.

At least four radars of a vital information acquisition apparatus may be located at four corners of the apparatus. FIG. 13 shows a schematic view of a vital information acquisition apparatus that employs four radars located at four corners of the apparatus. This arrangement enables long distance between radars, resulting in higher accuracy in subject localization using one of triangulation techniques.

Figure 14:
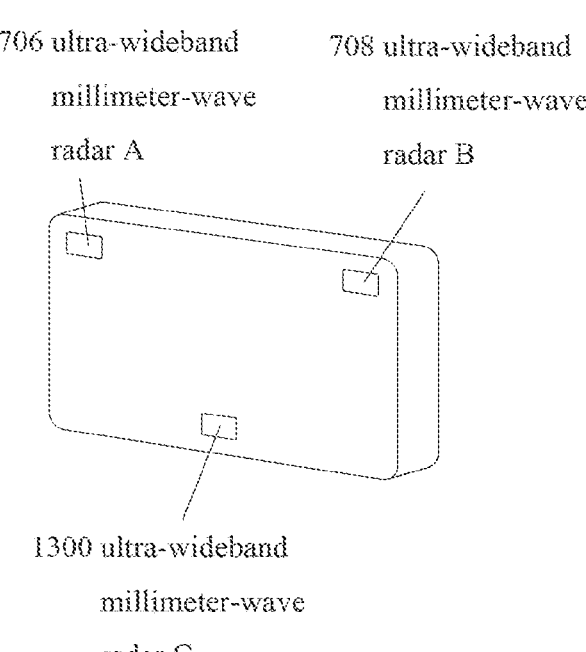
FIG. 14 is a schematic view of a vital information acquisition apparatus that employs three radars located in a triangular shape.

At least three radars of a vital information acquisition apparatus may be located in a triangular shape. FIG. 14 shows a schematic view of a vital information acquisition apparatus that employs three radars located in a triangular shape. This arrangement enables long distance between radars, resulting in higher accuracy in subject localization using one of triangulation techniques.

Figure 15:
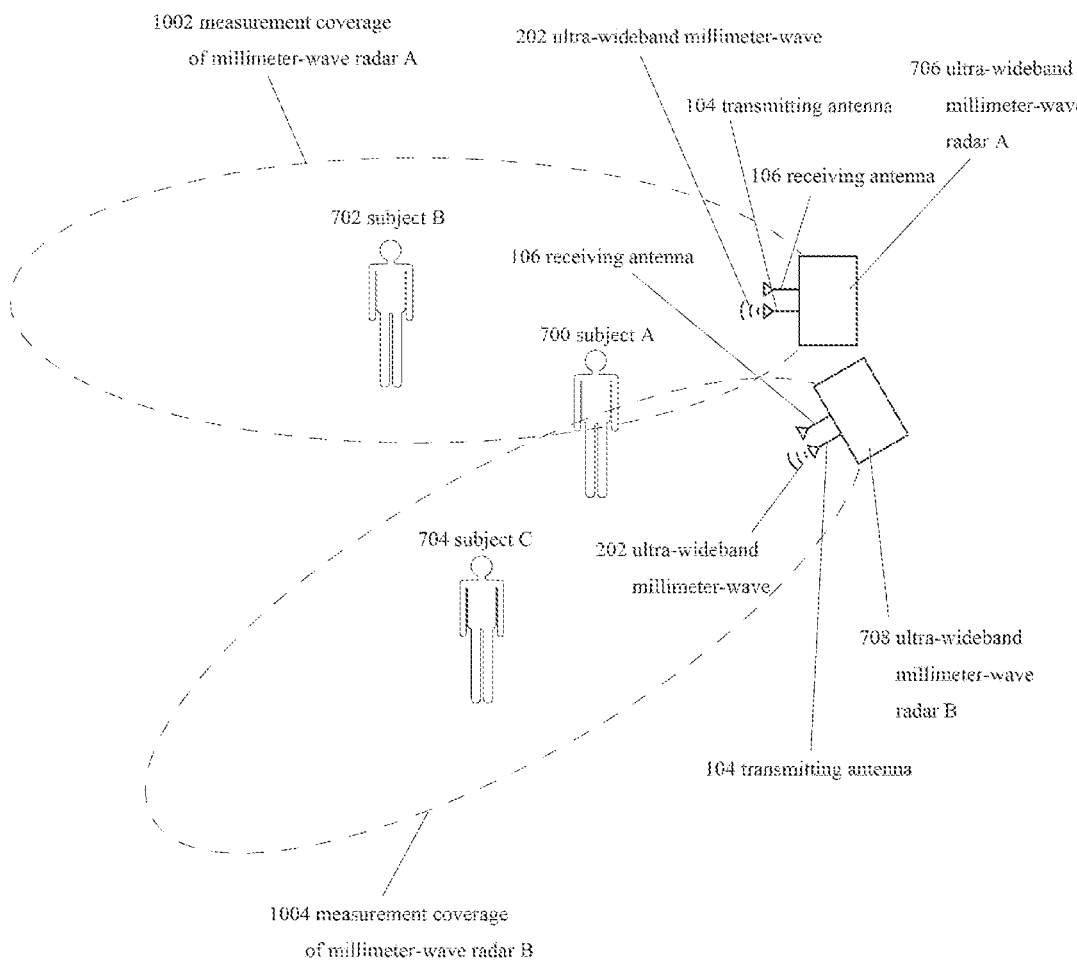
FIG. 15 is a schematic view of a vital information acquisition apparatus, wherein the measurement directions of different radars of a vital information acquisition apparatus is different.

The measurement directions of different radars of a vital information acquisition apparatus may be different, because this arrangement enables the measurement coverages of different ultra-wideband millimeter-wave radars partially overlapped even when the distance between radars is close, resulting in higher accuracy in subject localization using a power ratio table among all radars with respect to subject location. FIG. 15 shows a schematic view of a vital information acquisition apparatus, where the measurement directions of different radars of a vital information acquisition apparatus is different. In this arrangement, the signal power of subject A 700 is received by both radar A and radar B. The signal power of subject B 702 received by radar A 706 is much larger than that received by radar B 708, and the signal power of subject C 704 received by radar A 706 is much smaller than that received by radar B 708.

A vital information acquisition apparatus of an embodiment of the present invention may employ at least two radar sites in order to improve localization accuracy, because this setting enables long distance between radars and partial overlapped measurement coverage of different radars.

A vital information acquisition apparatus of an embodiment of the present invention may be installed in television, cell phone, or devices with charging function.

Vital information acquisition apparatus of an embodiment of the present invention transmits ultra-wideband millimeter-waves to at least one subject and estimates vital information of at least one subject, comprising: at least one ultra-wideband millimeter-wave radar which includes at least one transmitting antenna and at least one receiving antenna and is configured to transmit a plurality of ultra-wideband millimeter-waves to plural subjects and receive a plurality of ultra-wideband millimeter-waves reflected by the subjects; and a controller comprising circuitry configured to convert a plurality of received ultra-wideband millimeter-waves to a plurality of radar signals, store the radar signals, detect scatters, classify scatters to scatter clusters, and select at least one scatter cluster, estimate subject locations, and calculate biometric information, the scatter detection may employ threshold selection in terms of signal intensity, the scatter classification may employ one of clustering algorithms including density-based spatial clustering of applications with noise, and the cluster selection may use scatter density and/or distance between the scatter cluster and the radar. One example for scatter cluster selection may employ the scatter density and distance given by $$\frac{m_k}{r_k}, \tag{12}$$

where $m_k$ is scatter density of the k-th scatter cluster, $r_k$ is the average distance of the scatters belong to the k-th scatter cluster.

A vital information acquisition apparatus of an embodiment of the present invention may estimate the subject location by the center of gravity of the scatters which belong to the selected scatter cluster.

A vital information acquisition apparatus of an embodiment of the present invention may estimate subject location using the signal intensity of a scatterer and the distance between a scatter and the center of gravity of the scatters which belong to the selected scatter cluster, because the scatter with high signal intensity indicates that the scatter corresponds to the body surface of a subject, and the scatterer that corresponds to body surface is supposed to locate the center of gravity of the scatters which belong to the selected scatter cluster.

A vital information acquisition apparatus of an embodiment of the present invention may apply phase unwrapping to the radar signal of the selected scatter cluster. Most ultra-wideband millimeter-wave radar of the apparatus transmit plural equally spaced ultra-wideband millimeter-waves in order to measure the velocity of multiple objects. This set is usually called a frame. For example, the controller comprising circuitry of the apparatus calculates the phase of a radar signal of the selected scatter cluster at each frame using phase unwrapping, where the controller comprising circuitry apply phase unwrapping using the phases of the plural radar signals in the previous frame. The application of the phase unwrapping results in the suppression of the occurrence of aliasing.

The controller comprising circuitry of the present vital information acquisition apparatus may further be configured to calculate displacement of the body surface of at least one subject, apply one of low-pass filters or band-pass filters to the displacement, calculate baseline of the filtered displacement using one of smoothing filters, detect respiratory interval using the crossing points of the filtered displacement to the baseline, and calculate respiratory rate and/or heart rate; smoothing filters include moving average, low-pass filter, Kalman filter, exponential smoothing, Butterworth filter, average of maximum and minimum using a sliding window. One example of the average of maximum and minimum using a sliding window is given by $$d_{base}(t) = \left( \max_{t-T_1 < \tau < t+T_2} d(\tau) + \min_{t-T_1 < \tau < t+T_2} d(\tau) \right)/2, \quad (13)$$

where $d(t)$ is the displacement after the application of one of low-pass filters or band-pass filters, $d_{base}(t)$ is the baseline of the filtered displacement, and $T_1+T_2$ is the sliding window width.

The controller comprising circuitry of the present vital information acquisition apparatus may further be configured to calculate the frequency of the displacement at maximum power, one of low-pass filters or band-pass filters applied to the displacement passes at least the frequency of the displacement at maximum power.

The controller comprising circuitry of the present vital information acquisition apparatus may further be configured to calculate the frequency of the displacement at maximum power, and estimate respiratory interval from the frequency of the displacement at maximum power, the window width of the smoothing filter used to calculate baseline of the filtered displacement is equal or larger than the estimated respiratory interval. One example of the estimated respiratory interval from the frequency of the displacement at maximum power is the reciprocal number of the frequency of the displacement at maximum power. The window width of the smoothing filter used to calculate baseline of the filtered displacement may range from the estimated respiratory interval to twice the estimated respiratory interval.

The controller comprising circuitry of the present vital information acquisition apparatus may further be configured to calculate the fluctuation range of the displacement or filtered displacement, and judge that apnea or breath arrest occurs or the radar signal includes no respiratory signal, because the small fluctuation range of the displacement or filtered displacement indicates that there is no radar signal caused by body surface displacement originated from respiration.

The controller comprising circuitry of the present vital information acquisition apparatus may further be configured to extract part of the displacement with small fluctuation, apply one of band-pass filters to the extracted displacement, calculate baseline of the extracted filtered displacement using one of smoothing filters, detect heartbeat interval using the crossing points of the extracted filtered displacement to the baseline of the extracted filtered displacement, and calculate heart rate; smoothing filters include moving average, low-pass filter, Kalman filter, exponential smoothing, Butterworth filter, average of maximum and minimum using a sliding window.

The controller comprising circuitry of the present vital information acquisition apparatus may further be configured to estimate respiratory rate and/or heart rate from the median of respiratory intervals and/or the median of heartbeat intervals.

A vital information acquisition method of an embodiment of the present invention stores the radar signals, calculates the correlation between the radar signals acquired by different radars, detects identical subjects acquired by different radars, estimates subject locations, and calculates biometric information, the estimation of subject locations includes the employment of power ratio table among all or a part of radars with respect to subject location and the employment of triangulation using distance information of all or a part of radars.

A vital information acquisition method of an embodiment of the present invention stores the radar signals, detects scatters, classifies scatters to scatter clusters, selects at least one scatter cluster, estimates subject locations, and calculates biometric information; the scatter detection may employ threshold selection in terms of signal intensity, the scatter classification may employ one of clustering algorithms including density-based spatial clustering of applications with noise, and the cluster selection may use scatter density and/or distance between the scatter cluster and the radar.

A vital information acquisition method of an embodiment of the present invention stores the radar signals, detects scatters, classifies scatters to scatter clusters, selects at least one scatter cluster, estimates subject locations, and calculates biometric information; the scatter detection may employ threshold selection in terms of signal intensity, the scatter classification may employ one of clustering algorithms including density-based spatial clustering of applications with noise, and the cluster selection may use scatter density and/or distance between the scatter cluster and the radar, calculates displacement of the body surface of at least one subject, applies one of low-pass filters or band-pass filters to the displacement, calculates baseline of the filtered displacement using one of smoothing filters, detects respiratory interval using the crossing points of the filtered displacement to the baseline, and calculates respiratory rate; smoothing filters include moving average, low-pass filter, Kalman filter, exponential smoothing, Butterworth filter, average of maximum and minimum using a sliding window.

First Exemplary Embodiment

FIG. 9 shows a schematic diagram of a vital information acquisition apparatus that aligns coordinate systems of different ultra-wideband millimeter-wave radars and calculates biometric information. A vital information acquisition apparatus includes at least two ultra-wideband millimeter-wave radars 706 and 708. An ultra-wideband millimeter-wave radar includes at least one transmitting antenna 104 and at least one receiving antenna 106. Ultra-wideband millimeter-waves 202 are transmitted from transmitting antennas 104. Transmitted ultra-wideband millimeter-wave 202 can be modulated using one of pulse compression techniques, e.g. m-sequence. Transmitted ultra-wideband millimeter-waves are reflected at the body surfaces of plural subjects 700, 702 and 704. Reflected ultra-wideband millimeter-waves are received by receiving antennas 106. A system controller 110 comprising circuitry configured to convert a plurality of received ultra-wideband millimeter-waves 202 to a plurality of radar signals, store the radar signals 112, synthesize a virtual array radar from each ultra-wideband millimeter-wave radar with plural transmitting antennas and plural receiving antennas 900, construct complex or real radar image data using one of beamforming techniques 902, calculate the power of radar image data 904, calculate respiratory interval information 800, apply one of clustering techniques to the respiratory interval radar image data 906, detect identical subject positions acquired by different radars 606, and align measurement coordinate system of different ultra-wideband millimeter-wave radars 802, and calculate biometric information of all subjects 908. The parameter of $T_C$ in Equation (5) is 30 s and the parameter of $T_P$ in Equation (6) is 20 s.

Second Exemplary Embodiment

FIG. 10 shows a schematic diagram of a vital information acquisition apparatus, where the measurement coverages of different ultra-wideband millimeter-wave radars partially overlap. A vital information acquisition apparatus includes at least two ultra-wideband millimeter-wave radars 706 and 708. An ultra-wideband millimeter-wave radar includes one transmitting antenna 104 and one receiving antenna 106. Ultra-wideband millimeter-waves 202 are transmitted from transmitting antennas 104. Transmitted ultra-wideband millimeter-wave 202 can be modulated using one of pulse compression techniques, e.g. m-sequence. Transmitted ultra-wideband millimeter-waves are reflected at the body surfaces of plural subjects 700, 702 and 704. Reflected ultra-wideband millimeter-waves are received by receiving antennas 106. A system controller 110 comprising circuitry configured to convert a plurality of received ultra-wideband millimeter-waves 202 to a plurality of radar signals, store the radar signals 112, calculate the correlation of radar signals 604, detect identical subject acquired by different radars 1000, estimate subject location 1008, and calculate biometric information 908. Subject locations are estimated by the employment of power ratio table among all radars with respect to subject location 1006. In the case of FIG. 10, the signal power of subject A 700 is received by both radar A and radar B. The signal power of subject B 702 received by radar A 706 is much larger than that received by radar B 708, and the signal power of subject C 704 received by radar A 706 is much smaller than that received by radar B 708. The apparatus of an embodiment of the present invention detects the identical subjects acquired by different radars 606, and estimates their locations using a power ratio table among all radars with respect to subject location 1006.

Third Exemplary Embodiment

FIG. 11 shows a schematic diagram of a vital information acquisition apparatus that transmits ultra-wideband millimeter-waves to plural subjects and estimates vital information of plural subjects. A vital information acquisition apparatus includes at least two ultra-wideband millimeter-wave radars 706 and 708. An ultra-wideband millimeter-wave radar includes at least one transmitting antenna 104 and at least one receiving antenna 106. Ultra-wideband millimeter-waves 202 are transmitted from transmitting antennas 104. Transmitted ultra-wideband millimeter-wave 202 can be modulated using one of pulse compression techniques, e.g. m-sequence. Transmitted ultra-wideband millimeter-waves are reflected at the body surfaces of plural subjects 700, 702 and 704. Reflected ultra-wideband millimeter-waves are received by receiving antennas 106. A system controller 110 comprising circuitry configured to convert a plurality of received ultra-wideband millimeter-waves 202 to a plurality of radar signals, store the radar signals 112, calculate the correlation of radar signals acquired by different radars 604, detect identical subject acquired by different radars 1000, estimate subject location 1008, and calculate biometric information 908. An example of subject location estimation is the employment of power ratio table among all or a part of radars with respect to subject location 1006. Other example of subject location estimation is the employment of triangulation using distance information of all or a part of radars. Distance information may be calculated from time-of-flight information between each subject and each radar. In the case of FIG. 11, the signal power of subject A 700 is received by both radar A and radar B. The signal power of subject B 702 received by radar A 706 is much larger than that received by radar B 708, and the signal power of subject C 704 received by radar A 706 is much smaller than that received by radar B 708. The apparatus of an embodiment of the present invention detects the identical subjects acquired by different radars 1000, and estimates their locations using a power ratio table among all radars with respect to subject location 1006. The location of subject also may be calculated by the employment of the triangulation using distance information from at least two radars. For example, the two-dimensional location of subject B can be located by the employment of triangulation using the distance between radar A and subject B 1100 and the distance between radar B and subject B 1102. The three-dimensional location of each subject requires at least three radars by the employment of triangulation. The distance between each subject and each radar may be calculated by time-of-flight information. The triangulation, sometimes called 3D TOF (time-of-flight) is useful when the distance between radars is sufficiently longer than the measurement accuracy in distance between each subject and each radar.

Fourth Exemplary Embodiment

Vital information acquisition apparatus of an embodiment of the present invention transmits ultra-wideband millimeter-waves to at least one subject and estimates vital information of at least one subject, comprising: at least one ultra-wideband millimeter-wave radar which includes at least one transmitting antenna and at least one receiving antenna and is configured to transmit a plurality of ultra-wideband millimeter-waves to plural subjects and receive a plurality of ultra-wideband millimeter-waves reflected by the subjects; and a controller comprising circuitry configured to convert a plurality of received ultra-wideband millimeter-waves to a plurality of radar signals, store the radar signals, detect scatters, classify scatters to scatter clusters, and select at least one scatter cluster, estimate subject locations, and calculate biometric information, the scatter detection may employ threshold selection in terms of signal intensity, the scatter classification may employ one of clustering algorithms including density-based spatial clustering of applications with noise, and the cluster selection may use scatter density and/or distance between the scatter cluster and the radar.

Fifth Exemplary Embodiment

A controller comprising circuitry of the present vital information acquisition apparatus may further be configured to calculate displacement of the body surface of at least one subject, apply one of low-pass filters or band-pass filters to the displacement, calculate baseline of the filtered displacement using one of smoothing filters, detect respiratory interval using the crossing points of the filtered displacement to the baseline, and calculate respiratory rate and/or heart rate; smoothing filters include moving average, low-pass filter, Kalman filter, exponential smoothing, Butterworth filter, average of maximum and minimum using a sliding window. The sliding window width of the smoothing filter used to calculate baseline of the filtered displacement ranges from the estimated respiratory interval to twice the estimated respiratory interval. The estimated respiratory interval from the frequency of the displacement at maximum power is the reciprocal number of the frequency of the displacement at maximum power.

The present invention has the following aspects.

1. A vital information acquisition apparatus, comprising: a microwave radar system which includes at least one transmitting antenna and at least one receiving antenna and is configured to transmit a plurality of microwaves to a subject and receive a plurality of microwaves reflected by the subject; and a controller comprising circuitry configured to convert a plurality of received microwaves to a plurality of radar signals, store the radar signals, calculate the differential signals among the radar signals, calculate and evaluate the intensity of the differential signals, and estimate respiratory intervals, heartbeat intervals and/or position of the subject.

2. A vital information acquisition apparatus, comprising: an ultra-wideband millimeter-wave radar system which includes at least one transmitting antenna and at least one receiving antenna and is configured to transmit a plurality of ultra-wideband millimeter-waves to a subject and receive a plurality of ultra-wideband millimeter-waves reflected by the subject; and a controller comprising circuitry configured to convert a plurality of received ultra-wideband millimeter-waves to radar signals, store the radar signals, calculate the differential signals among the radar signals at each position, calculate and evaluate the intensity of the differential signals at each position, and estimate respiratory intervals, heartbeat intervals and/or position of the subject.

3. The vital information acquisition apparatus according to claim 2, wherein the controller comprising circuitry is configured to estimate respiratory intervals, heartbeat intervals, and/or position of the subject by the time difference which minimizes the intensity of the differential signals at each position.

4. The vital information acquisition apparatus according to claim 3, wherein the controller comprising circuitry is configured to estimate respiratory intervals of the subject by the time difference which minimizes the intensity of the differential signals at each position within the time difference from 0.2 to 10 s.

5. The vital information acquisition apparatus according to claim 3, wherein the controller comprising circuitry is configured to estimate heartbeat intervals of the subject by the time difference which minimizes the intensity of the differential signals at each position within the time difference from 0.1 to 2 s.

6. The vital information acquisition apparatus according to claim 3, wherein the controller comprising circuitry is configured to be input subject information, and cause the range of time difference for the minimization of the intensity of the differential signals to be adjusted to the subject.

7. The vital information acquisition apparatus according to claim 3, wherein the controller comprising circuitry is configured to apply at least one smoothing filter including median filter, moving average filter and Hampel filter to the intensity of the differential signals at each position in the time domain and/or in the spatial domain, to respiratory intervals and/or heartbeat intervals of the subject.

8. The vital information acquisition apparatus according to claim 3, wherein the controller comprising circuitry is configured to determine the subject is at a certain position when a large drop of the intensity of differential signal, respiratory interval, and/or heartbeat interval are detected at the position.

9. The vital information acquisition apparatus according to claims 1, 2 and 3, wherein the radar system includes a plurality of transmitting antennas and/or a plurality of receiving antennas and is configured to transmit a plurality of electromagnetic waves to a plurality of directions and/or receive a plurality of electromagnetic waves reflected from a plurality of directions; and the controller comprising circuitry is configured to estimate respiratory intervals, heartbeat intervals, and/or the position of at least one subject. 10. The vital information acquisition apparatus according to claims 1, 2 and 3, further comprising: a driving unit connected to the radar system, wherein the controller is configured to direct the transmitting antenna and receiving antenna to the measurement direction, and to estimate respiratory intervals, heartbeat intervals, and/or the position of at least one subject.

11. The vital information acquisition apparatus according to claims 1, 2 and 3, further comprising: a plurality of radar systems which include at least one transmitting antenna and at least one receiving antenna and are configured to transmit a plurality of electromagnetic waves to a plurality of positions and receive a plurality of electromagnetic waves reflected from a plurality of positions; and a controller comprising circuitry is configured to synchronize the radar systems, employ a frequency-division multiple access technique or code division multiple access, and cause to estimate respiratory intervals, heartbeat intervals and/or positions of a plurality of subjects without interference.

12. The vital information acquisition apparatus according to claims 2 and 3, wherein the controller comprising circuitry is configured to calculate variation of radar signals at each position, and determine the existence of breathing of the subject and/or the existence of a subject at the position using the variation of radar signals and/or the intensity of radar signals.

13. The vital information acquisition apparatus according to claims 2 and 3, wherein the controller comprising circuitry is configured to determine that the subject is in apnea or hypopnea when variation of radar signals decreases and/or when variation of the intensity of the differential signals in the time domain decreases.

14. The vital information acquisition apparatus according to claims 2 and 3, wherein the controller comprising circuitry is configured to determine that the subject is recovered from apnea or hypopnea when variation of radar signals increases and/or when variation of the intensity of the differential signals in the time domain increases.

15. The vital information acquisition apparatus according to claims 1, 2 and 3, wherein the controller comprising circuitry is configured to transmit vital information to at least one remote server including a remote data storage device in a cloud computing environment.

16. A vital information acquisition method that stores time-series data corresponding to vital information, calculates the differential signals, calculates and evaluates the differential signal intensity, and estimates respiratory intervals, heartbeat intervals, and/or position of a subject.

17. The vital information acquisition method according to claim 16, wherein the method estimates respiratory intervals, heartbeat intervals, and/or position of the subject by the time difference which minimizes the intensity of the differential signals.

18. The vital information acquisition method according to claims 16 and 17, wherein the method extracts a plurality of parts of the time-series data corresponding to vital information using one of window functions, including rectangular window, B-spline window, Hann window, Hamming window, and Tukey window.

19. The vital information acquisition method according to claims 16 and 17, wherein the method calculates variation of time-series data corresponding to vital information, and determines the existence of breathing of the subject and/or the existence of a subject using the variation and/or intensity of time-series data corresponding to vital information.

20. The vital information acquisition method according to claims 16, 17 and 19, wherein the method applies at least one smoothing filter including median filter, moving average filter and Hampel filter to the intensity of the differential signals at each position, respiratory interval of the subject, variation of time-series data corresponding to vital information, intensity of time-series data corresponding to vital information, and/or heartbeat interval of the subject in the time domain and/or in the spatial domain.

21. A vital information acquisition apparatus, comprising: at least two microwave radars each of which includes at least one transmitting antenna and at least one receiving antenna and is configured to transmit a plurality of microwaves to plural subjects and receive a plurality of microwaves reflected by the subjects; and a controller comprising circuitry configured to convert a plurality of received microwaves to a plurality of radar signals, store the radar signals, calculate the correlation between the radar signals acquired by different radars, and detect identical subject positions acquired by different radars.

22. A vital information acquisition apparatus, comprising: at least two ultra-wideband millimeter-wave radars each of which includes at least one transmitting antenna and at least one receiving antenna and is configured to transmit a plurality of ultra-wideband millimeter-waves to plural subjects and receive a plurality of ultra-wideband millimeter-waves reflected by the subjects; and a controller comprising circuitry configured to convert a plurality of received ultra-wideband millimeter-waves to a plurality of radar signals, store the radar signals, calculate the correlation between the radar signals acquired by different radars, and detect identical subject positions acquired by different radars.

23. The vital information acquisition apparatus, wherein the controller comprising circuitry is configured to synthesize a virtual array radar from each ultra-wideband millimeter-wave radar with plural transmitting antennas and plural receiving antennas.

24. The vital information acquisition apparatus, wherein the controller comprising circuitry is configured to construct complex or real radar image data using one of beamforming techniques, beamforming techniques includes Fourier transform application in the fast-time direction and Fourier transform application in the channel number domain of the virtual array when the vital information acquisition apparatus employs FMCW ultra-wideband millimeter-wave radars.

25. The vital information acquisition apparatus, wherein a controller comprising circuitry further configured to subtract the DC component of radar image data, the DC component of radar image data includes time average of radar image data.

26. The vital information acquisition apparatus, wherein a controller comprising circuitry further configured to detect plural human and/or animal target candidates and estimate their positions using radar image data.

27. The vital information acquisition apparatus, wherein a controller comprising circuitry further configured to construct respiratory image data from radar image data, the respiratory image data construction includes the band-path filter application to real radar image data, and band-path filter application to phase information of complex radar image data.

28. The vital information acquisition apparatus, wherein a controller comprising circuitry further configured to construct respiratory interval radar image data, the respiratory interval radar image data includes respiratory interval information at all or part of the coordinates of radar image data.

29. The vital information acquisition apparatus, wherein a controller comprising circuitry further configured to detect plural human and/or animal targets and estimate their positions using one of clustering techniques, the clustering techniques include X-means algorithm, k-means algorithm.

30. The vital information acquisition apparatus, wherein a controller comprising circuitry configured to apply one of clustering techniques to the respiratory interval radar image data acquired by each ultra-wideband millimeter-wave radar individually, and synthesize the clusters acquired by each respiratory interval radar image data.

31. The vital information acquisition apparatus, wherein a controller comprising circuitry configured to calculate the correlation between respiratory interval information at all clusters acquired by different radars.

32. The vital information acquisition apparatus, wherein a controller comprising circuitry configured to align the coordinates systems of different radars using at least two cluster pairs of different radars with highest correlation values of respiratory interval information.

33. The vital information acquisition apparatus, wherein a controller comprising circuitry configured to align the coordinates systems of different radars using two cluster pairs of different radars with highest correlation values of respiratory interval information, and align the coordinates systems of different radars using all cluster pairs of different radars, the alignment information acquired by two cluster pairs of different radars with highest correlation values of respiratory interval information is employed as the initial value for the alignment procedure using all cluster pairs of different radars.

34. The vital information acquisition apparatus, wherein a controller comprising circuitry configured to eliminate the cluster pair of different radars when the positions measured by different radars are distant. 35. A vital information acquisition apparatus, comprising: at least two ultra-wideband millimeter-wave radars each of which includes at least one transmitting antenna and at least one receiving antenna and is configured to transmit a plurality of ultra-wideband millimeter-waves to plural subjects and receive a plurality of ultra-wideband millimeter-waves reflected by the subjects; and a controller comprising circuitry configured to convert a plurality of received ultra-wideband millimeter-waves to a plurality of radar signals, store the radar signals, calculate the correlation between the radar signals acquired by different radars, and detect identical subjects acquired by different radars, estimate subject locations, and calculate biometric information, the estimation of subject locations includes the employment of power ratio table among all radars with respect to subject location.

36. The vital information acquisition apparatus, wherein at least one ultra-wideband millimeter-wave radar transmits and receives a plurality of ultra-wideband millimeter-waves with the sampling rate of 20 ms or less.

37. The vital information acquisition apparatus, wherein at least one ultra-wideband millimeter-wave radar transmits and receives a plurality of ultra-wideband millimeter-waves with the sampling rate from 1 to 20 ms.

38. A vital information acquisition method that stores the radar signals, calculates the correlation between the radar signals acquired by different radars, and detects identical subject position acquired by different radars.

39. A vital information acquisition method that stores the radar signals, calculates respiratory interval information, detects identical subject position acquired by different radars, and aligns measurement coordinate system of different ultra-wideband millimeter-wave radars.

40. A vital information acquisition method that stores the radar signals, calculates the correlation between the radar signals acquired by different radars, and detects identical subject position acquired by different radars, estimates subject location, and calculate biometric information, where the estimation of subject location includes the employment of power ratio table among all radars with respect to subject location.

41. A vital information acquisition apparatus, comprising: at least two ultra-wideband millimeter-wave radars each of which includes at least one transmitting antenna and at least one receiving antenna and is configured to transmit a plurality of ultra-wideband millimeter-waves to plural subjects and receive a plurality of ultra-wideband millimeter-waves reflected by the subjects; and a controller comprising circuitry configured to convert a plurality of received ultra-wideband millimeter-waves to a plurality of radar signals, store the radar signals, calculate the correlation between the radar signals acquired by different radars, detect identical subjects acquired by different radars, estimate subject locations, and calculate biometric information, the estimation of subject locations includes the employment of power ratio table among all or a part of radars with respect to subject location and the employment of triangulation using distance information of all or a part of radars.

42. A vital information acquisition apparatus, comprising: at least two ultra-wideband millimeter-wave radars each of which includes at least one transmitting antenna and at least one receiving antenna and is configured to transmit a plurality of ultra-wideband millimeter-waves to plural subjects and receive a plurality of ultra-wideband millimeter-waves reflected by the subjects; and a controller comprising circuitry configured to convert a plurality of received ultra-wideband millimeter-waves to a plurality of radar signals, store the radar signals, construct radar data at each distance, calculate the power of radar data, estimate respiratory information, apply one of clustering techniques to the respiratory interval radar data, detect identical subject acquired by different radars, estimate subject location, and calculate biometric information, the respiratory information estimation includes the band-path filter application to real radar data, and band-path filter application to phase information of complex radar image data, the respiratory interval radar data includes respiratory interval information at all or part of the distances of radar image data, and the clustering techniques include X-means algorithm, k-means algorithm.

43. The vital information acquisition apparatus, wherein the synchronization accuracy between radars is 1 ns or worse.

44. The vital information acquisition apparatus, wherein at least four radars are located at four corners of the apparatus.

45. The vital information acquisition apparatus, wherein at least three radars are located in a triangular shape.

46. The vital information acquisition apparatus, wherein the measurement directions of different radars are different.

47. The vital information acquisition apparatus, wherein at least two radar sites are employed.

48. The vital information acquisition apparatus, wherein the apparatus is installed in television, cell phone, or devices with charging function.

49. A vital information acquisition apparatus, comprising: at least one ultra-wideband millimeter-wave radar which includes at least one transmitting antenna and at least one receiving antenna and is configured to transmit a plurality of ultra-wideband millimeter-waves to at least one subject and receive a plurality of ultra-wideband millimeter-waves reflected by the subject; and a controller comprising circuitry configured to convert a plurality of received ultra-wideband millimeter-waves to a plurality of radar signals, store the radar signals, detect scatters, classify scatters to scatter clusters, select at least one scatter cluster, estimate subject locations, and calculate biometric information, the scatter detection may employ threshold selection in terms of signal intensity, the scatter classification may employ one of clustering algorithms including density-based spatial clustering of applications with noise, and the cluster selection may use scatter density and/or distance between the scatter cluster and the radar.

50. The vital information acquisition apparatus, wherein the subject location is estimated by the center of gravity of the scatters which belong to the selected scatter cluster.

51. The vital information acquisition apparatus, wherein the estimation of subject location may use the signal intensity of a scatterer and the distance between a scatter and the center of gravity of the scatters which belong to the selected scatter cluster.

52. The vital information acquisition apparatus, wherein the ultra-wideband millimeter-wave radar transmits plural ultra-wideband millimeter-waves at irregular intervals, and a controller comprising circuitry further configured to apply phase unwrapping to the radar signal of the selected scatter cluster.

53. The vital information acquisition apparatus, wherein the controller comprising circuitry further configured to calculate displacement of the body surface of at least one subject, apply one of low-pass filters or band-pass filters to the displacement, calculate baseline of the filtered displacement using one of smoothing filters, detect respiratory interval using the crossing points of the filtered displacement to the baseline, and calculate respiratory rate and/or heart rate; smoothing filters include moving average, low-pass filter, Kalman filter, exponential smoothing, Butterworth filter, average of maximum and minimum using a sliding window.

54. The vital information acquisition apparatus, wherein the controller comprising circuitry further configured to calculate the frequency of the displacement at maximum power, one of low-pass filters or band-pass filters applied to the displacement passes at least the frequency of the displacement at maximum power.

55. The vital information acquisition apparatus, wherein the controller comprising circuitry further configured to calculate the frequency of the displacement at maximum power, and estimate respiratory interval from the frequency of the displacement at maximum power, the window width of the smoothing filter used to calculate baseline of the filtered displacement is equal or larger than the estimated respiratory interval.

56. The vital information acquisition apparatus, wherein the controller comprising circuitry further configured to calculate the fluctuation range of the displacement or filtered displacement, and judge that apnea or breath arrest occurs or the radar signal includes no respiratory signal.

57. The vital information acquisition apparatus, wherein the controller comprising circuitry further configured to extract part of the displacement with small fluctuation, apply one of band-pass filters to the extracted displacement, calculate baseline of the extracted filtered displacement using one of smoothing filters, detect heartbeat interval using the crossing points of the extracted filtered displacement to the baseline of the extracted filtered displacement, and calculate heart rate; smoothing filters include moving average, low-pass filter, Kalman filter, exponential smoothing, Butterworth filter, average of maximum and minimum using a sliding window.

58. The vital information acquisition apparatus, wherein the controller comprising circuitry configured to estimate respiratory rate and/or heart rate from the median of respiratory intervals and/or the median of heartbeat intervals.

59. A vital information acquisition method that stores the radar signals, calculates the correlation between the radar signals acquired by different radars, detects identical subjects acquired by different radars, estimates subject locations, and calculates biometric information, the estimation of subject locations includes the employment of power ratio table among all or a part of radars with respect to subject location and the employment of triangulation using distance information of all or a part of radars.

60. A vital information acquisition method that stores the radar signals, detects scatters, classifies scatters to scatter clusters, selects at least one scatter cluster, estimates subject locations, and calculates biometric information; the scatter detection may employ threshold selection in terms of signal intensity, the scatter classification may employ one of clustering algorithms including density-based spatial clustering of applications with noise, and the cluster selection may use scatter density and/or distance between the scatter cluster and the radar.

61. A vital information acquisition method that stores the radar signals, detects scatters, classifies scatters to scatter clusters, selects at least one scatter cluster, estimates subject locations, and calculates biometric information; the scatter detection may employ threshold selection in terms of signal intensity, the scatter classification may employ one of clustering algorithms including density-based spatial clustering of applications with noise, and the cluster selection may use scatter density and/or distance between the scatter cluster and the radar, calculates displacement of the body surface of at least one subject, applies one of low-pass filters or band-pass filters to the displacement, calculates baseline of the filtered displacement using one of smoothing filters, detects respiratory interval using the crossing points of the filtered displacement to the baseline, and calculates respiratory rate and/or heart rate; smoothing filters include moving average, low-pass filter, Kalman filter, exponential smoothing, Butterworth filter, average of maximum and minimum using a sliding window.

Obviously, numerous modifications and variations of the present invention are possible in light of the above teachings. It is therefore to be understood that within the scope of the appended claims, the invention may be practiced otherwise than as specifically described herein.

REFERENCE SIGNS LIST

100 subject
102 microwave radar system
104 transmitting antenna
106 receiving antenna
108 microwave
110 system controller
112 store the radar signals
114 calculate the differential signals among the radar signals
116 calculate and evaluate the intensity of the differential signals
118 estimate respiratory intervals, heartbeat intervals, and position of the subject
200 ultra-wideband millimeter-wave radar system
202 ultra-wideband millimeter-wave
300 subject information
400 store time-series data corresponding to vital information
402 calculate the differential signals among the time-series data
404 calculate and evaluate the intensity of the differential signals among the time-series data
406 estimate respiratory intervals, heartbeat intervals, and position of the subject
500 extract a plurality of parts of time-series data
600 microwave radar A
602 microwave radar B
604 calculate the correlation of radar signals acquired by different radars
606 detect identical subject positions acquired by different radars
700 subject A
702 subject B
704 subject C
706 ultra-wideband millimeter-wave radar A
708 ultra-wideband millimeter-wave radar B
800 calculate respiratory interval information
802 align measurement coordinate system of different ultra-wideband millimeter-wave radars
900 synthesize a virtual array radar
902 construct complex or real radar image data
904 calculate the power of radar image data
906 apply one of clustering techniques to the respiratory interval radar image data
908 calculate biometric information of all subjects
1000 detect identical subject acquired by different radars
1002 measurement coverage of millimeter-wave radar A
1004 measurement coverage of millimeter-wave radar B
1006 power ratio table among all radars with respect to subject location
1008 estimate subject location
1100 distance between radar A and subject B
1102 distance between radar B and subject B

1200 construct complex or real radar data at each distance for each radar

1202 calculate the power of radar data

1300 ultra-wideband millimeter-wave radar C

1302 ultra-wideband millimeter-wave radar D

What is claimed is:

1. A vital information acquisition apparatus, comprising:

a microwave radar system which includes at least one transmitting antenna and at least one receiving antenna and is configured to transmit a plurality of microwaves to a subject and receive a plurality of microwaves reflected by the subject; and a controller comprising circuitry configured to convert a plurality of received microwaves to a plurality of radar signal data, store the radar signal data, calculate differential signals from the radar signal data, calculate and evaluate intensity of the differential signals, and estimate respiratory intervals, heartbeat intervals and/or position of the subject based on a time difference which minimizes the evaluated intensity within a physiological time range.

2. A vital information acquisition apparatus, comprising:

an ultra-wideband millimeter-wave radar system which includes at least one transmitting antenna and at least one receiving antenna and is configured to transmit a plurality of ultra-wideband millimeter-waves to a subject and receive a plurality of ultra-wideband millimeter-waves reflected by the subject; and a controller comprising circuitry configured to convert a plurality of received ultra-wideband millimeter-waves to radar signal data, store the radar signal data, calculate differential signals from the radar signal data at a position of the subject, calculate and evaluate intensity of the differential signals at the position of the subject, and estimate respiratory intervals, heartbeat intervals and/or the position of the subject based on a time difference which minimizes the evaluated intensity within a physiological time range.

3. The vital information acquisition apparatus according to claim 2, wherein the time difference minimizes the intensity of the differential signals at the position of the subject.

4. The vital information acquisition apparatus according to claim 3, wherein the controller comprising circuitry is configured to estimate the respiratory intervals of the subject by the time difference which minimizes the intensity of the differential signals at the position of the subject, and wherein the time difference is within a range from 0.2 to 10 s.

5. The vital information acquisition apparatus according to claim 3, wherein the controller comprising circuitry is configured to estimate the heartbeat intervals of the subject by the time difference which minimizes the intensity of the differential signals at the position of the subject, and wherein the time difference is within a range from 0.1 to 2 s.

6. The vital information acquisition apparatus according to claim 3, wherein the controller comprising circuitry is configured to receive input subject information, and allow a range of time difference for the minimization of the intensity of the differential signals to be adjusted to the subject by the received input subject information.

7. The vital information acquisition apparatus according to claim 3, wherein the controller comprising circuitry is configured to apply at least one smoothing filter including a median filter, a moving average filter and a Hampel filter to the intensity of the differential signals at each position in the time domain and/or in the spatial domain, to respiratory intervals and/or heartbeat intervals of the subject.

8. The vital information acquisition apparatus according to claim 3, wherein the controller comprising circuitry is configured to determine the subject is at a certain position when a threshold drop of the intensity of differential signal, respiratory interval, and/or heartbeat interval are detected at the position.

9. The vital information acquisition apparatus according to claim 2, wherein the radar system includes a plurality of transmitting antennas and/or a plurality of receiving antennas and is configured to transmit a plurality of electromagnetic waves to a plurality of directions and/or receive a plurality of electromagnetic waves reflected from a plurality of directions; and the controller comprising circuitry is configured to estimate respiratory intervals, heartbeat intervals, and/or the position of at least one subject.

10. The vital information acquisition apparatus according to claim 2, further comprising:

a driving unit connected to the radar system, the driving unit being configured to generate the transmitted plurality of microwaves, wherein the controller is configured to direct the transmitting antenna and receiving antenna to the measurement direction, and to estimate respiratory intervals, heartbeat intervals, and/or the position of at least one subject.

11. The vital information acquisition apparatus according to claim 2, further comprising:

a plurality of radar systems each which include at least one transmitting antenna and at least one receiving antenna and are configured to transmit a plurality of electromagnetic waves to a plurality of positions and receive a plurality of electromagnetic waves reflected from a plurality of positions, wherein the controller comprising circuitry is configured to synchronize the radar systems, employ a frequency-division multiple access technique or code division multiple access, and estimate respiratory intervals, heartbeat intervals and/or positions of a plurality of subjects without interference among the plurality of radar systems.

12. The vital information acquisition apparatus according to claim 2, wherein the controller comprising circuitry is configured to calculate variation of the plurality of radar signal data, and determine the existence of breathing of the subject and/or presence of the subject at the position based on the variation of the plurality of radar signal data and/or the intensity of the differential signals.

13. The vital information acquisition apparatus according to claim 2, wherein the controller comprising circuitry is configured to determine that the subject is in apnea or hypopnea when variation of the plurality of radar signal data decreases and/or when variation of the intensity of the differential signals in the time domain decreases.

14. The vital information acquisition apparatus according to claim 2, wherein the controller comprising circuitry is configured to determine that the subject is recovered from apnea or hypopnea when variation of the plurality of radar signal data increases and/or when variation of the intensity of the differential signals in the time domain increases.

15. The vital information acquisition apparatus according to claim 2, wherein the controller comprising circuitry is configured to transmit vital information to at least one remote server including a remote data storage device in a cloud computing environment.

16. A vital information acquisition method, comprising:

storing time-series data corresponding to vital information;

calculating differential signals based on the time-series data;

calculating differential signal intensity for evaluation; and estimating respiratory intervals, heartbeat intervals, and/ or position of a subject, based on a time difference which minimizes the evaluated intensity of the differential signals within a physiological time range.

17. The vital information acquisition method according to claim 16, wherein the estimating is conducted based on time difference which minimizes the intensity of the differential signals.

18. The vital information acquisition method according to claim 16, further comprising:

extracting a plurality of parts of the time-series data corresponding to vital information using one of window functions, including a rectangular window, a B-spline window, a Hann window, a Hamming window, and a Tukey window.

19. The vital information acquisition method according to claim 16, further comprising:

calculating variation of the time-series data corresponding to vital information; and determining existence of breathing of the subject and/or existence of a subject using the variation and/or intensity of time-series data corresponding to vital information.

20. The vital information acquisition method according to claim 16, further comprising:

applying at least one smoothing filter including a median filter, a moving average filter and a Hampel filter to the intensity of the differential signals at each position, respiratory interval of the subject, variation of the time-series data corresponding to vital information, intensity of time-series data corresponding to vital information, and/or heartbeat interval of the subject in the time domain and/or in the spatial domain.

* * * * *